(12) United States Patent
Fontein et al.

(10) Patent No.: US 9,795,541 B2
(45) Date of Patent: *Oct. 24, 2017

(54) USE OF FREE RADICALLY CURABLE COMPOSITIONS IN ADDITIVE MANUFACTURING METHODS

(71) Applicant: VOCO GmbH, Cuxhaven (DE)

(72) Inventors: Nils Fontein, Cuxhaven (DE); Gerrit Luebbe, Cuxhaven (DE); Daniel Oldenburger, Cuxhaven (DE); Manfred Thomas Plaumann, Cuxhaven (DE)

(73) Assignee: VOCO GmbH, Cuxhaven (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/937,544

(22) Filed: Nov. 10, 2015

(65) Prior Publication Data
US 2016/0128909 A1    May 12, 2016

(30) Foreign Application Priority Data
Nov. 11, 2014 (DE) .................. 10 2014 116 402

(51) Int. Cl.
    *A61K 6/083* (2006.01)
(52) U.S. Cl.
    CPC .................... *A61K 6/083* (2013.01)
(58) Field of Classification Search
    CPC ..................................................... A61K 6/083
    See application file for complete search history.

(56) References Cited

U.S. PATENT DOCUMENTS

| | | |
|---|---|---|
| 3,347,954 A | 10/1967 | Brederek et al. |
| 4,243,692 A | 1/1981 | Scholze et al. |
| 4,447,520 A | 5/1984 | Henne et al. |
| 4,522,693 A | 6/1985 | Henne et al. |
| 4,575,330 A | 3/1986 | Hull et al. |
| 4,710,523 A | 12/1987 | Lechtken et al. |
| 4,772,530 A | 9/1988 | Gottschalk et al. |
| 4,792,632 A | 12/1988 | Ellrich et al. |
| 4,868,091 A | 9/1989 | Boettcher et al. |
| 4,874,450 A | 10/1989 | Gottschalk et al. |
| 4,954,414 A | 9/1990 | Adair et al. |
| 5,055,372 A | 10/1991 | Shanklin et al. |
| 5,057,393 A | 10/1991 | Shanklin et al. |
| 5,063,257 A | 11/1991 | Akahane et al. |
| 5,100,929 A | 3/1992 | Jochum et al. |
| 5,112,884 A | 5/1992 | Hanke et al. |
| 5,399,770 A | 3/1995 | Leppard et al. |
| 5,472,991 A | 12/1995 | Schmitt et al. |
| 5,717,125 A | 2/1998 | Wolter et al. |
| 5,761,169 A | 6/1998 | Mine et al. |
| 5,847,025 A | 12/1998 | Moszner et al. |
| 5,877,232 A | 3/1999 | Storch et al. |
| 6,020,528 A | 2/2000 | Leppard et al. |
| 6,288,138 B1 | 9/2001 | Yamamoto et al. |
| 6,566,413 B1 | 5/2003 | Weinmann et al. |
| 6,852,822 B1 | 2/2005 | Bissinger et al. |
| 7,081,485 B2 | 7/2006 | Suh et al. |
| 7,148,382 B2 | 12/2006 | Wolf et al. |
| 7,214,726 B2 | 5/2007 | Qian et al. |
| 2002/0129736 A1 | 9/2002 | Bui et al. |
| 2003/0069326 A1 | 4/2003 | Stangel et al. |
| 2003/0166816 A1* | 9/2003 | Bissinger ............. A61K 6/0017 528/10 |
| 2003/0207235 A1* | 11/2003 | der Zel ................... A61C 5/10 433/223 |
| 2004/0097613 A1 | 5/2004 | Hecht et al. |
| 2004/0110864 A1 | 6/2004 | Hecht et al. |
| 2006/0247330 A1 | 11/2006 | Takano et al. |
| 2007/0027229 A1 | 2/2007 | Moszner et al. |
| 2007/0142495 A1* | 6/2007 | Neffgen ............... A61K 6/0017 523/116 |
| 2008/0277814 A1 | 11/2008 | Moszner et al. |

(Continued)

FOREIGN PATENT DOCUMENTS

| | | |
|---|---|---|
| DE | 1495520 A1 | 4/1969 |
| DE | 2758414 A1 | 7/1979 |

(Continued)

OTHER PUBLICATIONS

Huck-Jones, D. et al., "Chemische Identität einzelner Partikel" [Chemical Identity of Individual Particles], Nachrichten aus der Chemie, 62: 886-887 (Sep. 2014). See English MAT Translation.
Antonucci, J.M. et al., "Synthesis and Properties of a Polyfluorinated Prepolymer Multifunctional Urethane Methacrylate," Progress in Biomedical Polymers, C. G. Gebelein et al., (Editors), Plenum Press, NY, pp. 121-131 (1990).
Kuo, J. S. et al. "Evaluation of Siloxane Containing Dental Composites," Journal of Dental Research Abstracts, vol. 6A, Abstract No. 30, p. 178 (1985).

(Continued)

*Primary Examiner* — Michael Pepitone
(74) *Attorney, Agent, or Firm* — Armstrong Teasdale LLP

(57) ABSTRACT

The present invention relates to the use of free-radically curable compositions, comprising chain-like and/or cyclic and/or cage-type polysiloxanes substituted by free-radically polymerizable groups and having at least 3 silicon atoms and/or mixed forms thereof, disiloxanes substituted by free-radically polymerizable groups, optionally one, two, three or more free-radically curable monomers having no silicon atom, fillers, initiators and/or catalysts for free-radical polymerization, and also further customary additives, in additive manufacturing methods, preferably in stereolithography (SL) and digital light processing (DLP). The present invention further relates to the use of the cured free-radically curable compositions, preferably for production of dental products.

19 Claims, 1 Drawing Sheet

(56) References Cited

U.S. PATENT DOCUMENTS

| | | |
|---|---|---|
| 2008/0319127 A1 | 12/2008 | Wolter |
| 2009/0048366 A1 | 2/2009 | Torii et al. |
| 2009/0105367 A1 | 4/2009 | Vogt et al. |
| 2011/0082250 A1 | 4/2011 | Wolter |
| 2012/0082637 A1 | 4/2012 | Blomker et al. |
| 2012/0082954 A1 | 4/2012 | Blomker et al. |
| 2012/0082958 A1 | 4/2012 | Blomker et al. |
| 2012/0082959 A1 | 4/2012 | Blomker et al. |
| 2012/0083550 A1 | 4/2012 | Blomker et al. |
| 2012/0115108 A1 | 5/2012 | Blomker et al. |
| 2012/0123012 A1 | 5/2012 | Rheinberger et al. |
| 2014/0138864 A1 | 5/2014 | Plaumann et al. |
| 2014/0221521 A1 | 8/2014 | Wolter et al. |
| 2014/0249325 A1 | 9/2014 | Wolter et al. |
| 2015/0094397 A1 | 4/2015 | Lueck |
| 2015/0111176 A1 | 4/2015 | Wachter et al. |
| 2015/0342841 A1 | 12/2015 | Lubbe |

FOREIGN PATENT DOCUMENTS

| | | |
|---|---|---|
| DE | 3236026 A1 | 3/1984 |
| DE | 3801511 A1 | 7/1989 |
| DE | 3941629 A1 | 6/1990 |
| DE | 3903407 A1 | 8/1990 |
| DE | 4231579 A1 | 3/1993 |
| DE | 4133494 A1 | 4/1993 |
| DE | 4416857 C1 | 6/1995 |
| DE | 19708294 A1 | 9/1997 |
| DE | 19860364 C2 | 6/2000 |
| DE | 19934407 A1 | 1/2001 |
| DE | 19938463 A1 | 2/2001 |
| DE | 19950284 A1 | 4/2001 |
| DE | 69704623 T2 | 10/2001 |
| DE | 10114290 B4 | 10/2002 |
| DE | 10119831 A1 | 10/2002 |
| DE | 102014210432 A1 | 12/2005 |
| DE | 60116142 T2 | 7/2006 |
| DE | 102006019092 A1 | 3/2007 |
| DE | 60029481 T2 | 7/2007 |
| DE | 102006050153 A1 | 5/2008 |
| DE | 112006001049 T5 | 12/2008 |
| DE | 102007050763 A1 | 4/2009 |
| DE | 102012012346 A1 | 12/2013 |
| DE | 102013008176 A1 | 10/2014 |
| EP | 0007508 A2 | 2/1980 |
| EP | 0047902 A2 | 3/1982 |
| EP | 0057474 A2 | 8/1982 |
| EP | 0059451 A1 | 9/1982 |
| EP | 0073413 A2 | 3/1983 |
| EP | 0173567 A2 | 3/1986 |
| EP | 0184095 B1 | 6/1986 |
| EP | 0262629 B1 | 4/1988 |
| EP | 0366977 B1 | 5/1990 |
| EP | 0783880 B1 | 7/1997 |
| EP | 0948955 B1 | 10/1999 |
| EP | 0980682 B1 | 2/2000 |
| EP | 1236459 B1 | 9/2002 |
| EP | 1563821 A1 | 8/2005 |
| EP | 1685182 B1 | 8/2006 |
| EP | 1839640 B1 | 10/2007 |
| EP | 1872767 A1 | 1/2008 |
| EP | 1881010 A1 | 1/2008 |
| EP | 1905415 A1 | 4/2008 |
| EP | 2070506 A1 | 6/2009 |
| EP | 2070935 A1 | 6/2009 |
| EP | 2436363 A2 | 4/2012 |
| EP | 2436364 A2 | 4/2012 |
| EP | 2436365 A2 | 4/2012 |
| EP | 2436366 A2 | 4/2012 |
| EP | 2436668 A1 | 4/2012 |
| EP | 2450025 A1 | 5/2012 |
| WO | 9729901 A1 | 8/1997 |
| WO | 02085974 A1 | 10/2002 |
| WO | 02092021 A1 | 11/2002 |
| WO | 02092023 A1 | 11/2002 |
| WO | 2005011621 A1 | 2/2005 |
| WO | 2005084611 A1 | 9/2005 |
| WO | 2006111352 A1 | 10/2006 |
| WO | 2013041723 A1 | 3/2013 |
| WO | 2013053693 A1 | 4/2013 |
| WO | 2013153183 A2 | 10/2013 |

OTHER PUBLICATIONS

Liang, X. et al., "Synthesis of None Bisphenol A Structure Dimethacrylate Monomer and Characterization for Dental Composite Applications," Dental Materials, 30(8): 917-925 (2014).

Fouassier, J-P. et al. (editors), Radiation Curing in Polymer Science and Technology, Photoinitiating Systems, vol. II, Elsevier Applied Science, London, New York 1993, Table of Contents (6 pages).

Fouassier, J-P. "Photoinitiation, Photopolymerization and, Photocuring, Fundamentals and Applications," Hanser Publishers, Munich, Vienna, New York 1995, Table of Contents (7 pages).

Watts, D.C. et al., "Determination of Polymerization Shrinkage Kinetics in Visible-Light Cured Materials: Methods Development," Dental Materials, 7(4): 281-287 (1991).

Gebhard, A., "Generative Fertigungsverfahren," 4th edition, Carl Hanser Verlag, Munich 2013, Table of Contents (22 pages).

European Search Report for EP Application No. 15193618.4, dated Mar. 15, 2016.

European Search Report for EP Application No. 15193617.6, dated Mar. 15, 2016.

* cited by examiner

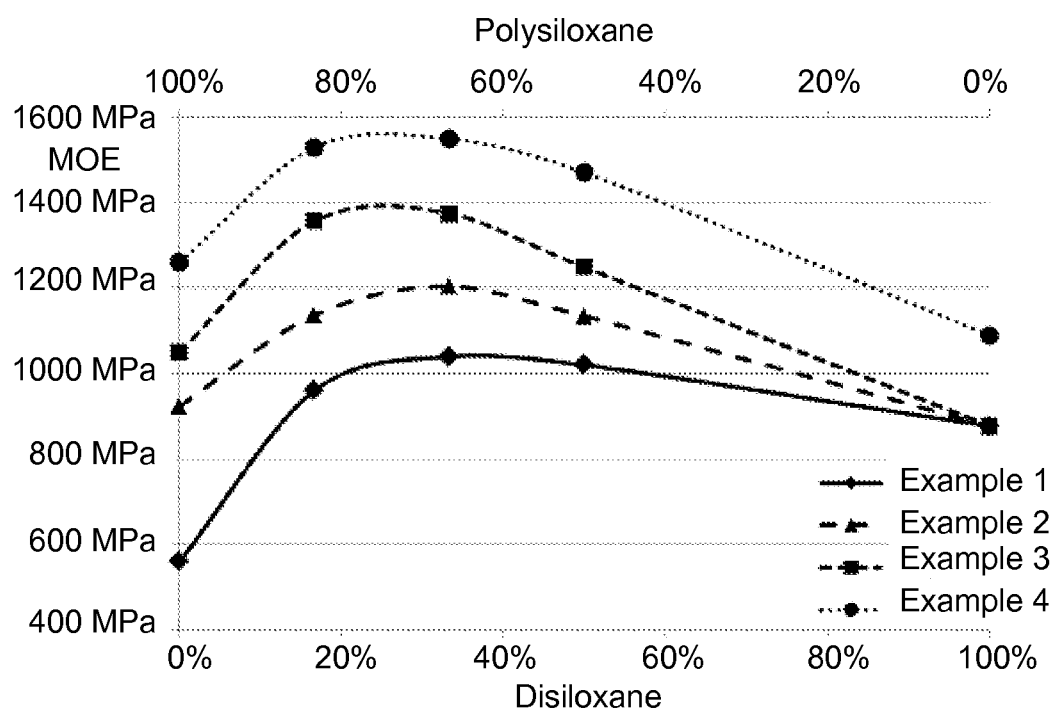

USE OF FREE RADICALLY CURABLE COMPOSITIONS IN ADDITIVE MANUFACTURING METHODS

CROSS-REFERENCE TO RELATED APPLICATIONS

This application claims priority to German Patent Application No. 102014116402.4, filed on Nov. 11, 2014, which is herein incorporated by reference in its entirety.

BACKGROUND OF THE DISCLOSURE

The present invention relates to the use of free-radically curable compositions, comprising chain-like and/or cyclic and/or cage-type polysiloxanes substituted by free-radically polymerizable groups and having at least 3 silicon atoms and/or mixed forms thereof, disiloxanes substituted by free-radically polymerizable groups, optionally one, two, three or more free-radically curable monomers having no silicon atom, fillers, initiators and/or catalysts for free-radical polymerization, and also further customary additives, in additive manufacturing methods, preferably in stereolithography (SL) and digital light processing (DLP). The present invention further relates to the use of the cured free-radically curable compositions, preferably for production of dental products.

Further aspects of the present invention and preferred configurations thereof will become apparent from the description which follows, the working examples and the claims.

The term "additive manufacturing method" is an established expression (see A. Gebhard, "Generative Fertigungsverfahren", 4th edition, Carl Hanser Verlag, Munich 2013) and is also known to those skilled in the art as "rapid prototyping" (RP). It describes, proceeding from a CAD dataset as a 3D geometry model, the layer-by-layer, tool-free formation of a particular shaped body.

The most commonly used RP method nowadays is stereolithography (see U.S. Pat. No. 4,575,330). This method works with an ultraviolet laser which cures suitable resin systems layer by layer. In general, conventional (meth) acrylate resins which have been provided with suitable photoinitiators are polymerized. A vertically movable platform having a suitable surface (metal, glass, ceramic, etc.) for the solid resin phase to grow onto is lowered to the distance of one layer thickness (20-50 μm), measured from the base of the liquid resin bath. Then there is localized crosslinking and curing of the resin by a laser, which is guided into the resin bath, for example, from beneath by means of micro-mirrors. The solid polymer that forms on the platform, after the crosslinking of a first resin layer, is moved up by one further layer thickness in the resin bath and hence covered again with liquid resin. The laser now cures the second layer. The sequence of raising the movable platform furnished with resin layers and the subsequent polymerization are repeated until the entire 3D model has been formed.

It is a characteristic feature of RP methods that the polymerizable groups are not completely converted during the layer-by-layer formation of the shaped body, and so the resulting parts still do not have sufficient final hardness and strength. The objects produced therefore have to be subjected to further curing in a further step of thermal aftertreatment in an oven or subsequent irradiation in a light box.

DLP is a modification of SL. Rather than a laser, in this method, visible non-coherent light is used for the polymerization of the curable resin. This methodology uses a projected image for selective polymerization of the resin. The pattern required is imaged directly onto the resin by a dynamic LCD mask, such that the entire layout is polymerized simultaneously, with curing of the exposed sites in the layer, leaving the unexposed sites uncured. Compared to curing by laser, which is effected only at particular points, this method is therefore much faster than SL.

Further RP methods are polyjet technology, the galvanometer-type scanning method, micro-stereolithography, multijet modeling, selective laser sintering, 3D printing, fused deposition modeling, 3D plotting, laminated object manufacturing or film transfer imaging.

Because of the versatility of the RP methods and the advantage of these methods compared to material-removing manufacturing methods, for example in terms of the more efficient production and the almost unlimited geometric freedom of the components and moldings, RP is becoming established in entire fields of industry, such as jewelry, architecture, design, medical technology, and here especially also in dentistry, where absolutely correct impression and duplicating methods are of course important.

For example, in dentistry, the procedure begins with the digital recording of the situation in the mouth by the 3D scan of a prepared cavity, in order thus to manufacture a dental molding on the basis of CAD (computer-aided design) data. The model generated is subsequently produced by using a shaping method, for example stereolithography, layer by layer from a liquid or pasty resin. Dental shaped bodies, such as inlays, onlays, veneers, crowns, bridges, artificial teeth, dentures, scaffolds, temporary prostheses and orthodontic products, can be manufactured directly in the dental practice (or in the dental laboratory) without any great effort or material loss (as occurs in the machining of blanks). The methods proceed in a simple and rapid manner, and they can even simultaneously manufacture several moldings/components from different orders.

Additive manufacturing methods, specifically including stereolithography methods, for production of dental shaped bodies are known from the prior art.

DE 697 04 623 T2 specifies a method for producing a three-dimensional article from a curable liquid medium, wherein the article is formed layer by layer, by each time applying a layer of liquid medium to a carrier and/or an already formed part of the article in a vessel containing liquid medium and then curing said layer.

WO 2013/153183 A2 describes composite resin compositions and methods for production of dental components by means of stereolithography. What is claimed is the use of a dental composition comprising a polyreactive binder, two photopolymerization initiators having different absorption maxima and an absorber.

DE 199 38 463 A1 discloses compositions curable with visible light, containing 2%-99% by weight of a curable resin, 0.01%-7% by weight of an initiator, 0%-5% by weight of a coinitiator and 0%-85% by weight of one or more modifiers such as fillers, dyes, pigments, flow improvers, thixotropic agents, polymeric thickeners, oxidizing additives, stabilizers and retardants for use in a shaping method. Methods are specified for microconsolidation, RP, film casting, the production of sintered polymer components, microstructuring, photolithography, the production of dental products, the production of surgical implants and/or the production of otoplastic products. The application document describes and depicts the structure of a stereolithography apparatus. In the inventive examples, filler-free free-radically curable compositions based on a mixture of butane-1, 4-diol dimethacrylate, aliphatic diurethane methacrylate and aliphatic urethane methacrylate, and a mixture of butane-1,4-diol dimethacrylate, aliphatic diurethane methacrylate, aliphatic urethane methacrylate and tetraethoxylated bisphenol A dimethacrylate are used.

DE 199 50 284 A1 is for the most part identical to the above-cited DE 199 38 463 A1. However, in this application document, additional free-radically curable systems from the publications DE 41 33 494 C2 and DE 39 03 407 A1, based on polysiloxanes, are integrated into the application text. However, this application document does not contain inventive compositions comprising polysiloxanes in form of examples.

DE 101 14 290 B4 is aimed at 3D plotting (an alternative method to stereolithography) for production of dental moldings, wherein curable resins from nozzles are applied to a suitable construction platform. This document also mentions silicone resins which lead to polymer networks through condensation or hydrolysis as resin systems.

DE 10 2012 012 346 A1 relates to shaped bodies made from dental material that remains soft, especially a gingival mask, and methods for production thereof by means of RP. The shaped body made from dental material that remains soft, especially the gingival mask or relining for a dental prosthesis, is said to be curable layer by layer to give an elastomer by means of an RP method involving light curing of a radiation-curable composition, especially by means of UV-A and/or UV-B rays. With particular preference, it is said to be possible to use compositions comprising radiation-curable silicones which may contain further auxiliaries, fillers, pigments or thinners. In this context, silicones functionalized with at least two alkene groups in a hydrosilylation reaction and hydridic silicones having at least two Si—H functionalities can be converted in the presence of a hydrosilylation catalyst. Alternatively, it is also said to be possible to use silanol-terminated polysiloxanes and silane crosslinking agents selected from vinyltrimethoxysilane, vinyltriaminosilane, vinyltriamidosilane, vinyltrioximosilane, vinyltriiso-propenoxysilane or vinyltriacetoxysilane and a photoinitiator.

The silanes specified in DE 199 34 407 A1 are said to have low viscosity and be flexible, which can be processed alone or together with other hydrolyzable, condensable and/or polymerizable components to give silicic acid polycondensates or to give silicic acid heteropolycondensates, the ultimate curing of which is then to be effected by polymerization of the C═C double bonds. The hydrolyzable and condensable silanes according to the invention are intended for use in specific applications, for example the coating of substrates of metal, plastic, paper, ceramic (by dipping, casting, painting, spraying, electrostatic spraying, electrocoating), for production of optical, optoelectronic and electronic components, for production of fillers, for production of scratch-resistant, abrasion-resistant anticorrosion coatings of shaped bodies, for example by injection molding, casting, pressing, rapid prototyping or extrusion, or for production of composites, for example with fibers, fillers or woven fabrics. As well as the fields of use of optics, electronics, medicine, especially dentistry and optoelectronics, the field of food packaging is also mentioned.

As a result of the method operations, the resin systems from the prior art used in additive manufacturing methods, for example in stereolithography, lack the desired precision in the geometric configuration of the shaped bodies. This is because the use of a radiation source in the layer-by-layer polymerization of the resin, through scattered and/or deflected photons, also results in concomitant curing of regions outside the defined shape. In order to minimize dimensional inaccuracy, what are called "absorbers" are generally added to the free-radically curable compositions. These are molecules which absorb radiation. In the literature, these compounds are also known as stabilizers or inhibitors. In general, benzotriazoles, triazines, benzophenones are used. Mention should also be made of salicylic acid derivatives and the hindered amine light stabilizers (HALS). Inorganic salts such as nanoscale titanium dioxide or zinc oxides can also assume a radiation-absorbing function. Their use can greatly improve dimensional accuracy, but this addition also reduces the through-curing depth and the conversion during free-radical curing.

It was therefore an object of the invention to provide a resin system having much higher dimensional accuracy in an additive manufacturing method, for example stereolithography. In addition, the resin system should also exhibit improved biocompatibility compared to conventional binders. Furthermore, the resin systems of the invention should have very good wettability on different substrates, a high conversion rate, a low water absorption, good mechanical strength and exceptionally low shrinkage.

SUMMARY OF THE DISCLOSURE

According to the invention, the stated object is achieved through the use of free-radically curable compositions comprising a.) chain-like and/or cyclic and/or cage-type polysiloxanes substituted by free-radically polymerizable groups and having at least 3 silicon atoms and/or mixed forms thereof, b.) disiloxanes substituted by free-radically polymerizable groups and having the following structure:

$R^1_a R^2_{(3-a)} Si-O-SiR^2_{(3-b)} R^1_b$ with $R^2$: alkyl, alkenyl, aryl, alkylaryl, arylalkyl, wherein different $R^2$ may be the same or different, $R^1$: YZ, Z: free-radically polymerizable group selected from the structural elements —O—(C═O)—CH═CH$_2$, —O—(C═O)—C(CH$_3$)═CH$_2$, 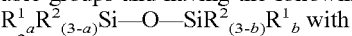 —(C═O)—C(CH$_3$)═CH$_2$, —CH═CH$_2$, —C(CH$_3$)═CH$_2$, —NH—(C═O)—CH═CH$_2$ and —NH—(C═O)—C(CH$_3$)═CH$_2$, wherein different Z may be the same or different, a: 1 or 2, b: 1 or 2, Y: a connecting element which links the silicon atom to the free-radically polymerizable group and consists of an alkylene group, wherein the alkylene group is an unsubstituted, linear, straight-chain or branched hydrocarbyl chain or wherein the alkylene group is an unsubstituted hydrocarbyl group interrupted by a urethane group, urea group, ester group, thiourethane group or amide group or wherein the alkylene group is a hydrocarbyl group substituted by a hydroxyl group and/or this hydroxyl group has been esterified or etherified or wherein the alkylene group is a hydrocarbyl group interrupted by an oxygen atom and/or nitrogen atom and/or sulfur atom and/or ester groups and/or thioester groups and substituted by a hydroxyl group and/or this hydroxyl group has been esterified or etherified and wherein different Y may be the same or different and wherein Y contains 20 or fewer carbon atoms and wherein YZ is chosen such that Z always has a maximum number of atoms,
c.) optionally one, two, three or more free-radically curable monomers having no silicon atom,
d.) 85 percent by weight or less of fillers based on the total weight of the free-radically curable dental composition,
e.) initiators and/or catalysts for the free-radical polymerization and
f.) further customary additives in additive manufacturing methods.

The use of a preferred composition of the invention in additive manufacturing methods involves the use of a composition free-radically curable in a light-induced manner.

The use of a particularly preferred composition in additive manufacturing methods involves the use of a free-radically curable composition as defined above, wherein the polysiloxanes (a.) are obtained by hydrolysis or partial hydrolysis and subsequent condensation or co-condensation of one, two, three or more compounds $R^1_a R^2_b SiX_c$ with X: halogen or alkoxy,
$R^2$: alkyl, alkenyl, aryl, alkylaryl, arylalkyl, wherein different $R^2$ may be the same or different,
$R^1$: YZ,
Z: free-radically polymerizable group selected from the structural elements —O—(C=O)—CH=CH$_2$, —O—(C=O)—C(CH$_3$)=CH$_2$, —(C=O)—CH=CH$_2$, —(C=O)—C(CH$_3$)=CH$_2$, —CH=CH$_2$, —C(CH$_3$)=CH$_2$, —NH—(C=O)—CH=CH$_2$ and —NH—(C=O)—C(CH$_3$)=CH$_2$,
wherein different Z may be the same or different,
a: 1 or 2,
b: 0 or 1,
c: 2 or 3,
a+b+c=4,
Y: a connecting element which links the silicon atom to the free-radically polymerizable group and consists of an alkylene group,
wherein the alkylene group is an unsubstituted, linear, straight-chain or branched hydrocarbyl chain or
wherein the alkylene group is an unsubstituted hydrocarbyl group interrupted by a urethane group, urea group, ester group, thiourethane group or amide group or
wherein the alkylene group is a hydrocarbyl group substituted by a hydroxyl group or this hydroxyl group has been esterified or etherified or
wherein the alkylene group is a hydrocarbyl group interrupted by an oxygen atom and/or nitrogen atom and/or sulfur atom and/or ester groups and/or thioester groups and substituted by a hydroxyl group or this hydroxyl group has been esterified or etherified and
wherein different Y may be the same or different and
wherein Y contains 20 or fewer carbon atoms and
wherein YZ is chosen such that Z always has a maximum number of atoms.

BRIEF DESCRIPTION OF THE DRAWINGS

FIG. 1 is a graph showing the moduli of elasticity of Examples 1-4.

DETAILED DESCRIPTION OF THE DISCLOSURE

Polysiloxane compounds having at least 3 silicon atoms for the purposes of the present text have at least one chain or a plurality of chains having alternating and mutually connected silicon atoms and oxygen atoms, wherein the chains are also linked to form rings of different size, or to form even more extensive structures such as cages, and wherein organic groups (organic side chains) are bonded to the silicon atoms. These organic groups may be of chemically very different composition and hence lead to a multitude of polysiloxane compounds having different properties. Frequently, these organic groups have one or more organically polymerizable groups (i.e. reactive groups) which can react with, for example, one or more organically polymerizable groups in another polysiloxane compound and hence form crosslinked polymerized polysiloxane compounds. Chain, ring and cage structures may also occur in the form of mixed structures. They are likewise part of the dental compositions of the invention.

Polysiloxane compounds have long been known and are obtainable, for example, by hydrolysis and condensation of silanes having hydrolyzable groups (see, for example, DE 27 58 414 A1) or by hydrosilylation of allyl or vinyl compounds with SiH-containing compounds. Polysiloxane compounds can be processed further to give a multitude of products, for example overlayers, coatings, membranes or bulk materials. This further processing is frequently based on a crosslinking reaction of organically polymerizable groups in the polysiloxane compounds (e.g. (meth)acrylate groups) and the resulting formation of crosslinked polysiloxane compounds.

"(Meth)acryl . . . " is understood in the context of the present text to mean both "acryl . . . " and "methacryl . . . ".

A specific group of polysiloxane compounds contains, in the organic groups (side chains), as well as an organically polymerizable group, additional free polar functional groups, for example hydroxyl or carboxyl groups.

For instance, DE 44 16 857 C1 relates to hydrolyzable and polymerizable silanes, to processes for preparation thereof and to the use thereof for production of silica (hetero) polycondensates and (hetero)polymers. Hydrolyzable, organically modified silanes find wide use in the production of scratch-resistant coatings for a wide variety of different substrates, for the production of fillers, of adhesives and sealing compounds or of shaped bodies. These systems are also said—like the systems from DE 199 34 407 A1 which has already been cited above—to be suitable for RP use.

DE 44 16 857 C1 discloses the use of silica (hetero)-polycondensates (polysiloxane compounds) in curable dental materials. The polysiloxane compounds described here comprise free polar functional groups (e.g. carboxyl or hydroxyl groups) capable of complexing suitable metal ions/transition metal ions (e.g. ions of titanium, zirconium or tin).

DE 198 60 364 C2 relates to polymerizable dental compositions based on siloxane compounds that are capable of curing, and to the use and production thereof. This publication describes the preparation of cyclic polysiloxanes and the use thereof as a basis for polymerizable compositions. In spite of high density of groups capable of polymerization, they are said to have a low viscosity which enables high filler loading, which leads to compositions having low polymerization shrinkage. Here too, free polar functions are present as well as the polymerizable units in the organic side chains of the polysiloxanes described.

The free polar functional groups, for example in the aforementioned polysiloxane compounds, however, regularly lead to unwanted properties too. For instance, it has been found that the hydrophilicity of the polysiloxane compounds caused by the (free) polar functional groups leads to increased water absorption in the presence of moisture, which reduces the wet strength of the curable material in a disadvantageous manner. Probably due to formation of internal hydrogen bonds, there is an increase in viscosity. This then has an adverse effect on handling in the production of the curable compositions.

There is a considerable need to adapt polysiloxane compounds further to the demands on a modern (curable or cured) material and to minimize or to eliminate the aforementioned disadvantages. Polysiloxane compounds adapted in such a way should have improved physical properties, for example lower polymerization shrinkage on polymerization/crosslinking of the polysiloxane compounds (i.e. on curing), increased strength and/or restricted water absorption with simultaneously comfortable consistency and viscosity of the curable material.

The first successes in the improvement of the polysiloxanes were achieved through addition or substitution of different substrates onto the free polar functionalities of the above-described specific polysiloxanes.

EP 1 874 847 B1 relates to a process for preparing silanes having two, three or even more structural units linked to one another by a urethane-, acid amide- and/or carboxylic ester-containing bridge, each of which contains at least one organically polymerizable radical and at least one silyl radical. These silanes should especially be suitable for modification of the properties of silicic acid (hetero)polycondensates and silyl-containing organic polymers. The process disclosed should also be suitable for bridging of already precondensed silicic acid (hetero)polycondensates.

The silicic acid (hetero)polycondensates (polysiloxane compounds) disclosed in EP 1 874 847 B1 have a free hydroxyl group (i.e. a free polar functional group). These free hydroxyl groups can react with a dicarboxylic acid derivative or diisocyanate such that hydroxyl groups form a link (bridge) with a dicarboxylic acid derivative or diisocyanate. Such linked polysiloxane compounds have a much higher molecular weight without any significant reduction in the double bond density (as a result of the organically polymerizable (meth)acrylate groups). Double bond density is understood here to mean the quotient of the number of polymerizable double bonds in a compound and the molecular weight of this compound. The higher molecular weight has a positive effect on biocompatibility and polymerization shrinkage on crosslinking of the linked polysiloxane compounds. At the same time, the hydrophobicity of the polysiloxane compounds was increased. However, it has been found that the higher molecular weight has an adverse effect on the viscosity of the linked polysiloxane compounds. The viscosity rises markedly with the degree of crosslinking, i.e. with the molecular weight, such that there is no longer satisfactorily tolerable processability in manufacturing a corresponding curable material comprising such linked polysiloxane compounds, even at quite a low degree of linkage.

EP 1 685 182 B1 relates to silanes and silicic acid polycondensates and partial condensates formed therefrom, in which an organic radical bonded to a silicon is present, which is branched and bears an independently organically polymerizable group at each of the two branches, or bears such a group at one of the two branches and has a radical having a further silicon atom at the other.

The polysiloxane compounds disclosed in EP 1 685 182 B1 also comprise free polar functional groups in the form of hydroxyl groups. By reaction of carboxylic acid or isocyanate derivatives which themselves likewise comprise polymerizable double bonds (e.g. (meth)acrylate groups), it is thus possible to link organically polymerizable groups onto free polar functional groups. These reaction products regularly have elevated strength with simultaneously increased hydrophobicity and improved biocompatibility due to the elevated molecular weight.

However, in these cases too, it has been shown that the introduction of additional polymerizable double bonds leads to increased polymerization shrinkage on crosslinking of the polysiloxane compounds, since the double bond density is markedly increased, but the increase in the molecular weight is only comparatively small.

WO 2013/041723 A1 discloses hydrolyzable and polymerizable silanes (including silicic acid polycondensates, i.e. siloxanes) having adjustable spatial distribution of the functional groups, and the use thereof. The teaching disclosed in WO 2013/041723 A1 relates to a method for chain extension of radicals bonded to silicon via carbon in silanes or siloxanes.

WO 2013/053693 A1 discloses silicic acid polycondensates (siloxanes) having cyclic olefin-containing structures and methods for preparation thereof, and the use thereof. WO 2013/053693 A1 discloses that polymer materials having moduli of elasticity adjustable within wide limits combined with high elastic strain (i.e. without brittleness) and hence high fracture toughness can be produced from silicic acid (hetero)polycondensates having cyclic olefin-containing structures.

The as yet unpublished DE 10 2014 210 432 describes polysiloxane compounds which have the aforementioned disadvantages from the prior art in a curable or cured composition at least only in attenuated form, if at all. The conceptual approach to these systems is based on the idea of converting the free functional group in the silane such that no additionally polymerizable double bonds are introduced into the system. Instead, hydrocarbyl radicals of high molecular weight having at least 11 carbon atoms are incorporated into the system. Surprising findings in the case of these curable compositions were a good viscosity of the polysiloxane compounds (the viscosity should be 50 Pa*s or less at a temperature of 25° C.) and an associated excellent processability in the production of a curable material containing the polysiloxane compounds, good hydrophobicity, good strength, especially good flexural strength, very low polymerization shrinkage on crosslinking of the polysiloxane compounds, i.e. on curing of the curable material, and good biocompatibility.

The measures taken in DE 10 2014 210 432 thus solved several problems at once:

Elimination of polar functional groups prevented the formation of intermolecular interactions. It was thus possible to keep the viscosity of the system at a comparatively low level in spite of a remarkable increase in molecular weight.

Incorporation of hydrocarbyl radicals of relatively high molecular weight resulted in widening of intramolecular spacing in the polysiloxane structure, and so it was possible to increase the accessibility of the free-radically polymerizable groups during the curing and hence to optimize the conversion rate. How else could one explain the fact that in these systems, with a comparatively reduced double bond density, the strength of the materials, for example the flexural strength of the cured dental compositions, remains at a very good level and in many cases is actually increased compared to the polysiloxanes without further conversion.

The increase in molecular weight with the same functionality, i.e. in the case of an effective lowering of the double bond density, made it possible to adjust especially what is perhaps the most important technical parameter for a curable composition, namely the value of the volume shrinkage during the curing, to an extremely low value.

Incorporation of hydrocarbyl residues of relatively high molecular weight also made the polysiloxane structure comparatively hydrophobic, such that the unwanted absorption of water now adopts extremely low values.

In in-house studies, it has now been found that further tremendous improvements in free-radically curable compositions containing polysiloxanes, specifically both the novel polysiloxanes from DE 10 2014 210 432 and the above-described systems from the prior art, are possible when free-radically polymerizable disiloxanes are added thereto. It has now been found that, surprisingly, the use of such compositions in additive manufacturing methods, for example stereolithography, can improve accuracy in the formation of the shaped bodies to a quite tremendous degree.

The use of disiloxanes in free-radically curable compositions, having a chemical structure based on the conventional crosslinking "monomers" such as bis-GMA (2,2-bis [p-(2'-hydroxy-3'-methacryloyloxypropoxy)phenyl] propane), UDMA (1,6-bis(methacryloyloxy-2-ethoxycarbonylamino)-2,4,4-trimethylhexane), TEGDMA (triethylene glycol dimethacrylate), HEDMA (hexanediol dimethacrylate), etc., is known from the prior art.

In a publication entitled "Synthesis and properties of a polyfluorinated prepolymer multifunctional urethane acrylate" (J. M. Antonucci, J. W. Stansbury, S. Venz, "Polymeric Materials Science and Engineering", 59, 388-396 (1988)), in which what are called "low surface energy resins" are examined, bis(methacryloyloxy-propyl)tetramethyldisiloxane (BIS-MPTMS) is used together with triethylene glycol dimethacrylate (TEGDMA) and hexamethylene 1,6-dimethacrylate (HEDMA) as organic resin matrix in a composite composition in the form of a powder/liquid system. On page 390, in the paragraph "Formulation of composites", it is stated that BIS-MPTMS is an excellent agent for reducing viscosity and has a voluminous flexible structure. It is said to be miscible with many resins over a wide concentration range.

In an abstract entitled "Evaluation of siloxane containing dental composites" (J. S. Kuo, J. M. Antonucci, W. Wu, "Journal of Dental Research Abstracts", 6A, and Abstract No. 30 (1985)), BIS-MPTMS is used together with Bis-GMA and UDMA as organic resin matrix. Here too, it is stated that BIS-MPTMS is miscible with the customary base monomers over a wide range (10%-50% by weight). The conclusion of this study reads: "Mechanical properties of the siloxane-containing composites were almost comparable to the controls, but, significantly, had reduced WS (water sorption) and enhanced OER (oral environmental resistance)."

In a more recent publication entitled "Synthesis of none bisphenol A structure dimethacrylate monomer and characterization for dental composite applications" (X. Liang, F. Liu, J. He, "Dental Materials", 30, 917-925 (2014)), the reaction product (SiMA) of the ring-opening addition reaction between 1,3-bis[2-(3,4-epoxy-cyclohex-1-yl)ethyl]tetramethyldisiloxane and methacrylic acid as a bis-GMA alternative was examined together with TEGDMA as organic matrix in dental composites. The authors conclude that the "study of SiMA based resin and composite material showed that SiMA had potential to be used in clinic, but mechanical properties of SiMA based resin and composite needed to be improved . . . " (page 923, point 5, "conclusion").

None of these documents suggest the use of free-radically curable compositions comprising the combination of chain-like and/or cyclic and/or cage-type polysiloxanes substituted by free-radically polymerizable groups and having at least 3 silicon atoms and/or mixed forms thereof with disiloxanes substituted by free-radically polymerizable groups and having the structure identified above in additive manufacturing methods.

Constituent a—chain-like and/or cyclic and/or cage-type polysiloxanes substituted by free-radically polymerizable groups and having at least 3 silicon atoms and/or mixed forms thereof.

Chain-like and/or cyclic and/or cage-type polysiloxanes substituted by free-radically polymerizable groups and having at least 3 silicon atoms and/or mixed forms thereof can be synthesized via the sol-gel process by controlled hydrolysis and condensation of appropriately functionalized derivatives of alkoxides of silicon or of halosilanes. These production methods have been described many times in the literature. In general, such a synthesis proceeds from a standard silane, for example isocyanatopropyldiethoxysilane, which is reacted in a first step, likewise in a standard reaction, for example in an isocyanate-alcohol polyaddition, for example with glycerol 1,3-dimethacrylate, to give the corresponding urethane. The compound obtained here consists on the one hand of the silicon atom which is furnished with hydrolyzable and condensable groups and is linked via a spacer consisting of an alkyl group (here a propyl group) and a urethane group as structural connecting element to a further functional structural segment, in this case to two free-radically polymerizable methacrylate groups. Such a simple synthesis method can be modified in various ways, since the possible reactions between appropriately functionalized silanes and suitable reactants seem unlimited. There is a correspondingly large number of synthesis suggestions in the literature. The starting compound thus comprises an inorganically condensable structural element, a variable connecting element and a free-radically crosslinkable organic base structure. In a catalytically controlled hydrolysis and condensation, the polysiloxane is obtained as an inorganic condensate substituted by free-radically polymerizable groups. Whether the polycondensate is in the form of chains, rings or three-dimensional cage forms, or in the corresponding mixed forms, depends on the exact conditions of the condensation. These include not only the reaction conditions (pH, amount of solvent and water, type and amount of catalyst, reaction temperature, manner of processing, etc.) but also the structural forms of the starting silane, significant factors being the number of alkoxy groups, the number of free-radically polymerizable groups, the chemical nature of the connecting element and the chain length of the spacer. Details of this can be found both in the scientific literature and in the patent literature.

The polysiloxanes, being a link between inorganic and organic chemistry, have exceptional material properties. Since they are additionally physiologically inert, i.e. have no significant toxicity, they are especially important for applications in medicine. The reason why polysiloxanes are virtually nontoxic is the low biological attackability of the silicon-carbon bonds and the restricted ability of the highly hydrophobic polymer chains to diffuse through cell membranes, which is why they should be particularly suitable for implantation (in teeth).

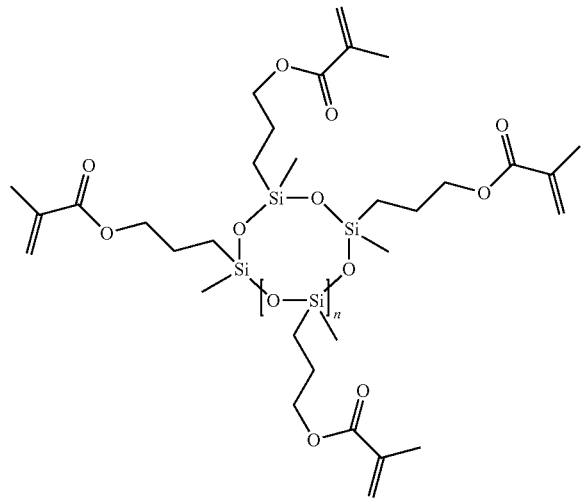

1

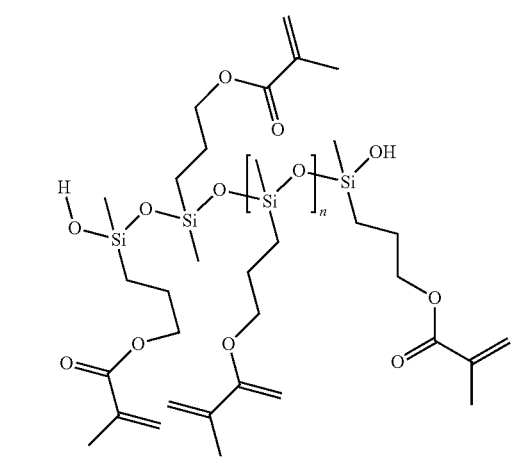

2

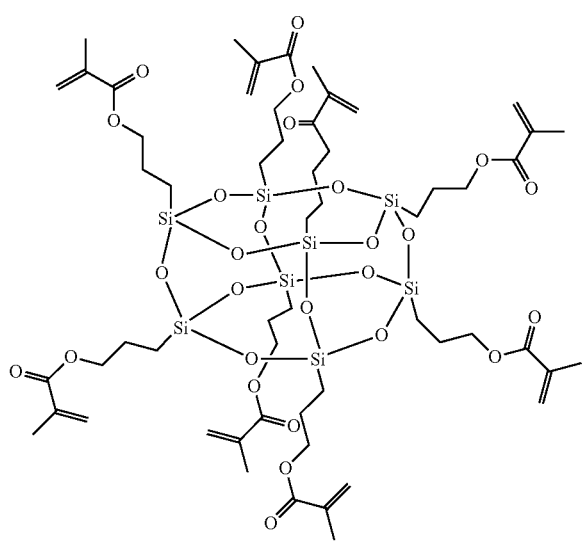

3

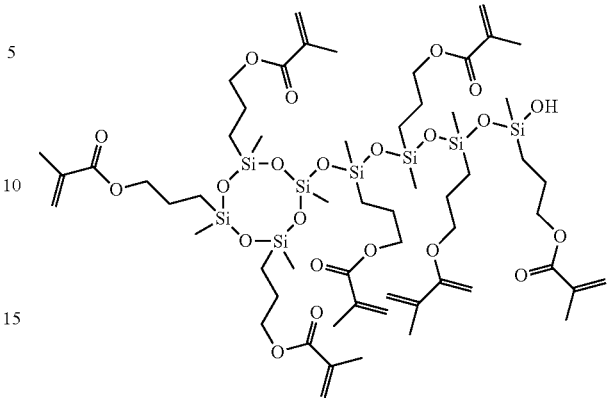

4

Constituent b—disiloxanes substituted by free-radically polymerizable groups and having the following structure:
$R^1_a R^2_{(3-a)} Si—O—SiR^2_{(3-b)} R^1_b$ with
$R^2$: alkyl, alkenyl, aryl, alkylaryl, arylalkyl, wherein different $R^2$ may be the same or different,
$R^1$: YZ,
Z: free-radically polymerizable group selected from the structural elements —O—(C=O)—CH=CH$_2$, —O—(C=O)—C(CH$_3$)=CH$_2$, —(C=O)—CH=CH$_2$, —(C=O)—C(CH$_3$)=CH$_2$, —CH=CH$_2$, —C(CH$_3$)=CH$_2$, —NH—(C=O)—CH=CH$_2$ and —NH—(C=O)—C(CH$_3$)=CH$_2$,
wherein different Z may be the same or different,
a: 1 or 2,
b: 1 or 2,
Y: a connecting element which links the silicon atom to the free-radically polymerizable group and consists of an alkylene group,
wherein the alkylene group is an unsubstituted, linear, straight-chain or branched hydrocarbyl chain or
wherein the alkylene group is an unsubstituted hydrocarbyl group interrupted by a urethane group, urea group, ester group, thiourethane group or amide group or
wherein the alkylene group is a hydrocarbyl group substituted by a hydroxyl group and/or this hydroxyl group has been esterified or etherified or
wherein the alkylene group is a hydrocarbyl group interrupted by an oxygen atom and/or nitrogen atom and/or sulfur atom and/or ester groups and/or thioester groups and substituted by a hydroxyl group and/or this hydroxyl group has been esterified or etherified and
wherein different Y may be the same or different and
wherein Y contains 20 or fewer carbon atoms and
wherein YZ is chosen such that Z always has a maximum number of atoms.

Disiloxanes are characterized by exceptional chain mobility, since the compounds have free rotation about the silicon-oxygen bonds, one reason for which is the difference in size between the oxygen atom and the silicon atom. This leads to compounds having a remarkably low viscosity because of the flexibility of the structure thereof. In addition, the shielding of the oxygen atoms by the hydrocarbyl groups on the silicon leads to marked hydrophobicity and to greatly restricted interaction of the chains with one another, such that the wetting of surfaces should be favored.

As well as some commercially available inventive disiloxanes (e.g. 1,3-bis(3-methacryloyloxypropyl)tetramethyldisiloxane, 1,3-bis(3-methacryloyloxy-2-hydroxypropoxypropyl)tetra-methyldisiloxane, 1,3-bis-[(acryloyloxymethyl)phenethyl]tetramethyldisiloxane), there are numerous synthesis strategies for preparation of the inventive disiloxanes.

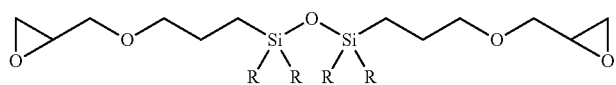
5
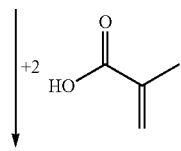
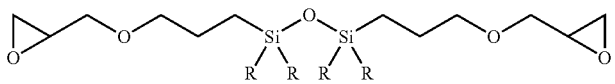
6
1,3-Bis(3-methacryloyloxy-2-hydroxypropoxypropyl) disiloxane 6 can be prepared by reaction of the corresponding 1,3-bis(3-glycidoxypropyl)disiloxane 5 with methacrylic acid.
5
+2 EtOH
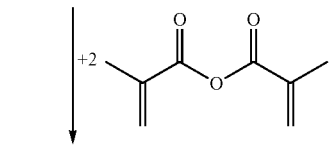
7
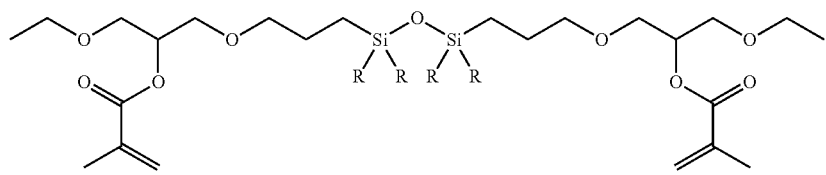
8
The disiloxane 8 can be synthesized from 1,3-bis(3-glycidoxypropyl)disiloxane 5 by reaction with ethanol and then methacrylic anhydride.

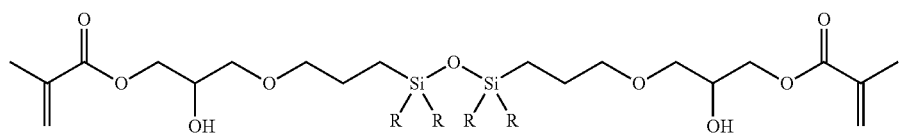
6
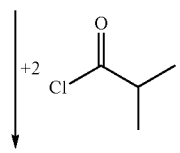
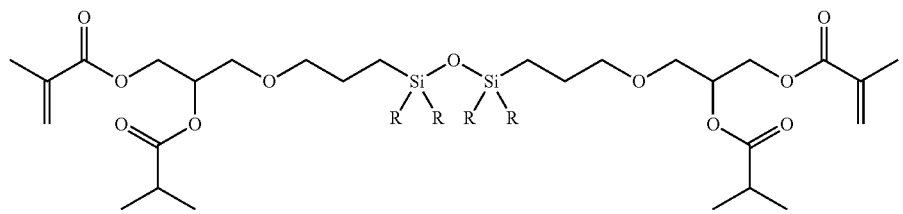
9
It is possible to prepare the corresponding disiloxanes 9, 10, 11, 12 and 13 from 1,3-bis(3-methacryloyloxy-2-hydroxypropoxypropyl)disiloxane 6 by further reaction with different acid chlorides or anhydrides.
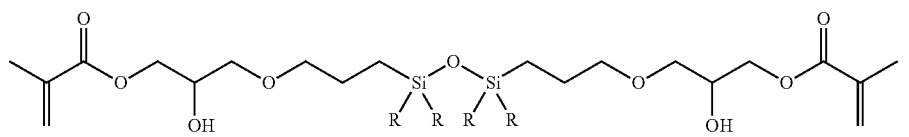
6
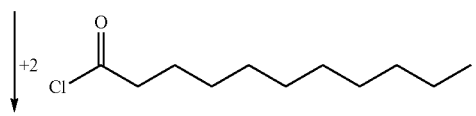
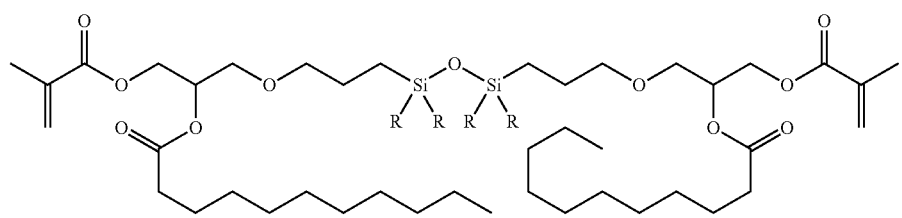
10

-continued
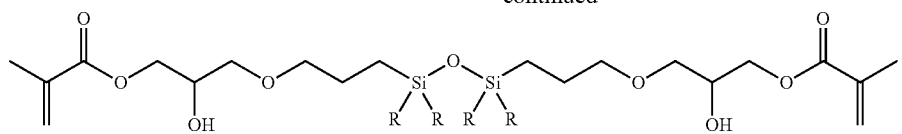
6
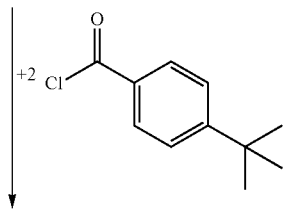
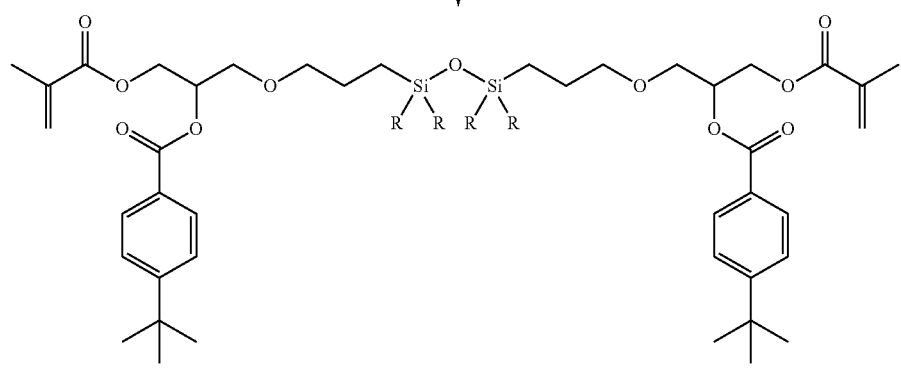
11
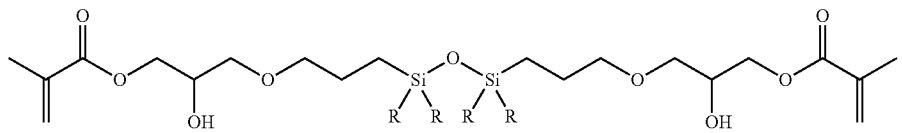
6
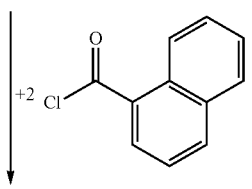
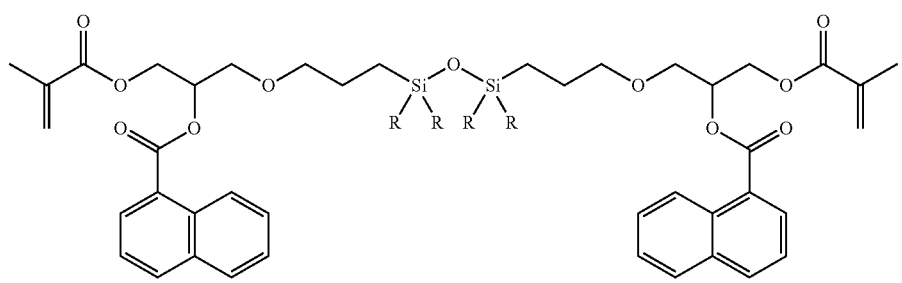
12

-continued
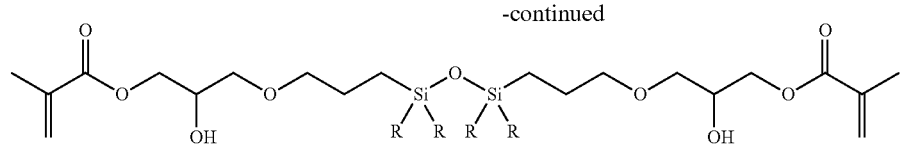
6
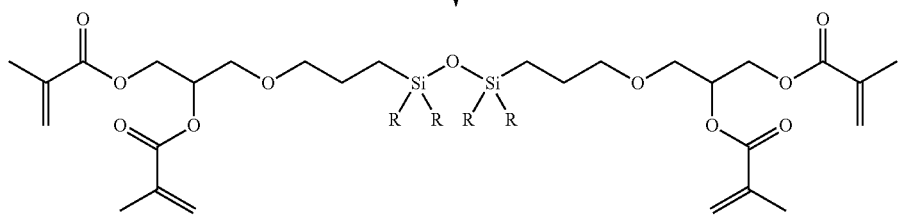
13
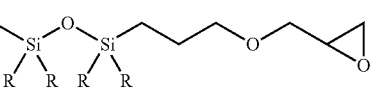
5
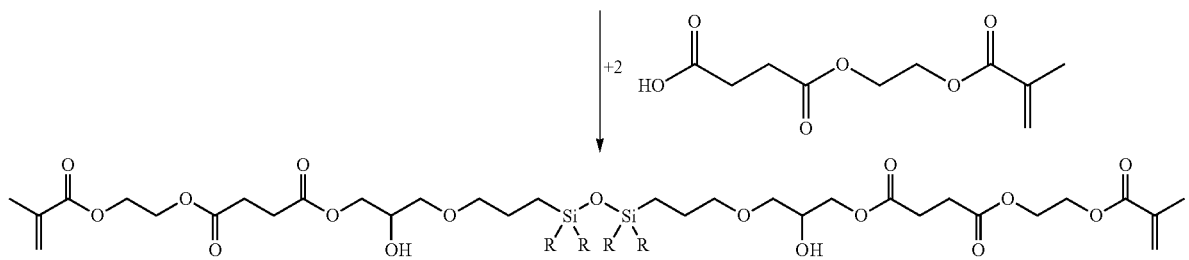
14
It is also possible to synthesize the corresponding disiloxane 14 from 1,3-bis(3-glycidoxypropyl)disiloxane 5 by reaction with mono(2-methacryloyloxyethyl) succinate.
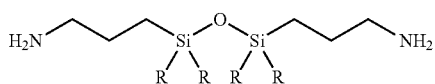
15
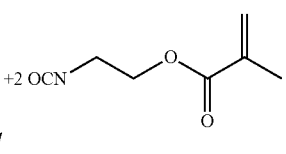

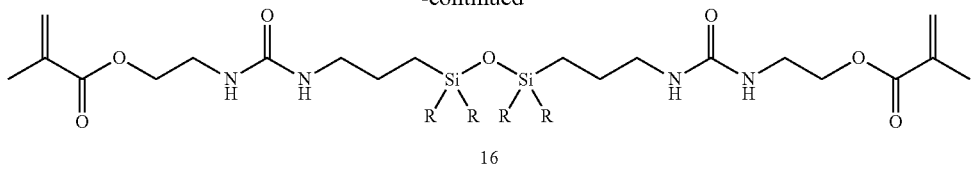
16
The corresponding urea derivative 16 is obtained from commercially available 1,3-bis(3-aminopropyl)disiloxane 15 by reaction with 2-isocyanatoethyl methacrylate.
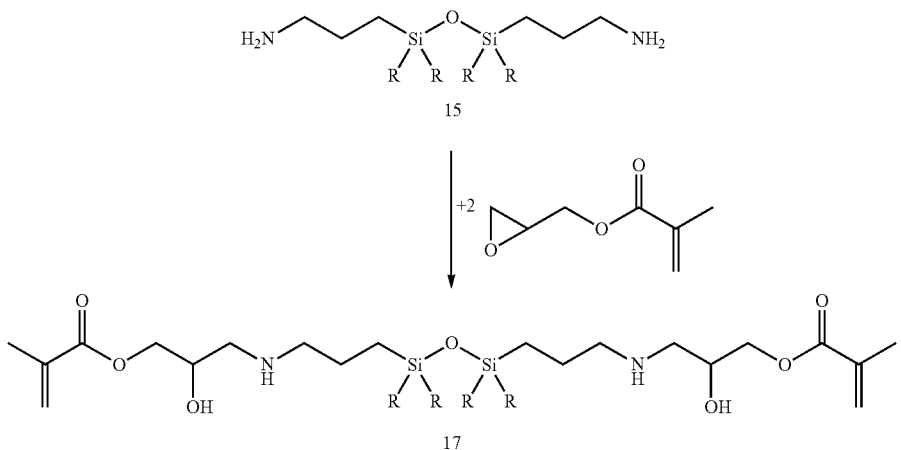
It is possible to prepare the corresponding disiloxanes 17 and 18 from 1,3-bis(3-aminopropyl)disiloxane 15 by reaction with, respectively, 2 and 4 equivalents of glycidyl methacrylate.
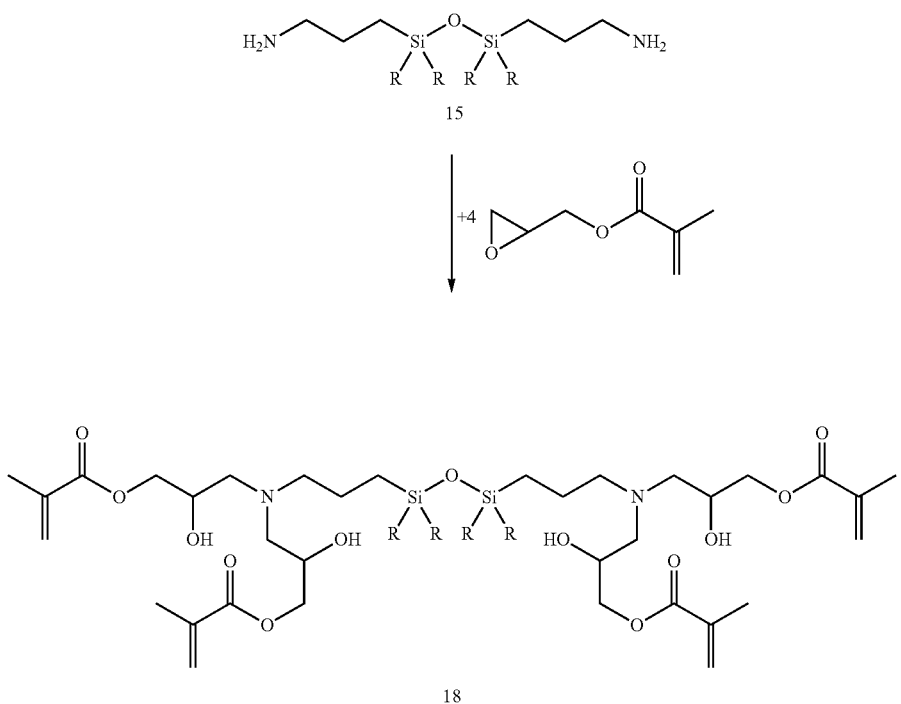

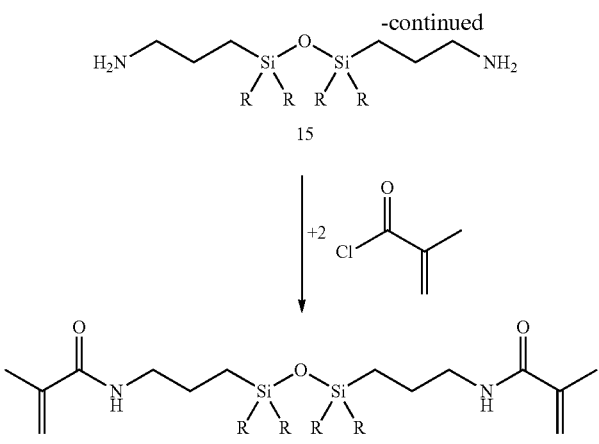
1,3-Bis(3-methacrylamidopropyl)disiloxane 19 is likewise obtainable from 1,3-bis(3-aminopropyl)disiloxane 15 by reaction with methacryloyl chloride.
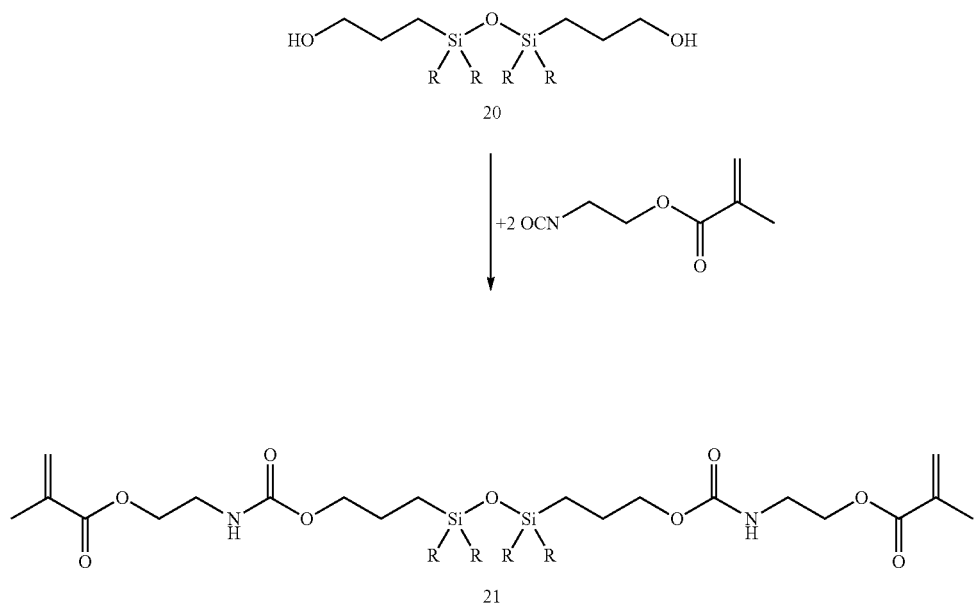
The corresponding urethane derivative 21 is obtained from commercially available 1,3-bis(3-hydroxy-propyl)disiloxane 20 by reaction with 2-isocyanatoethyl methacrylate.
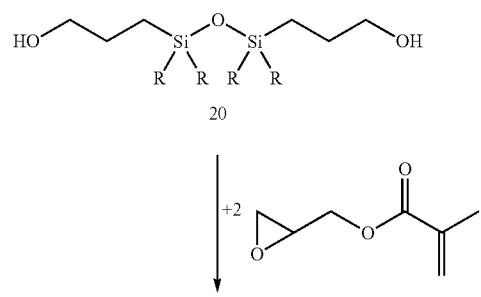

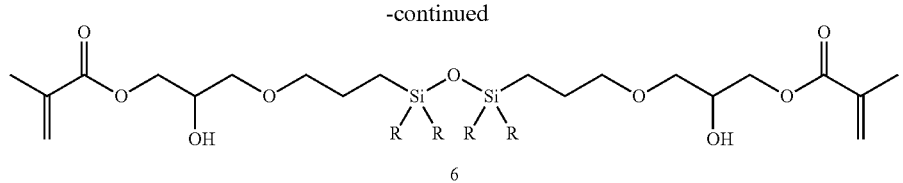

6

The corresponding 1,3-bis(3-methacryloyloxy-2-hydroxy-propoxypropyl)disiloxane 6 is also obtainable in turn from 1,3-bis(3-hydroxypropyl)disiloxane 20 by reaction with glycidyl methacrylate.

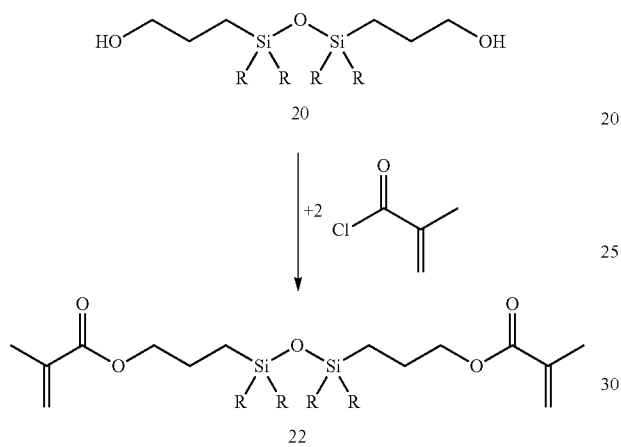

The corresponding 1,3-bis(3-methacryloyloxypropyl)-disiloxane 22 is likewise obtained from 1,3-bis(3-hydroxypropyl)disiloxane 20 by reaction with methacryloyl chloride.

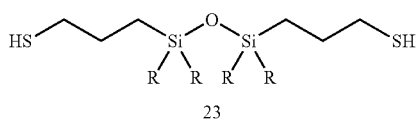

23

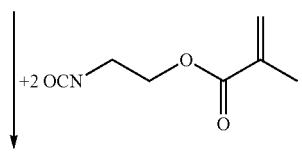

24

The corresponding thiourethane derivative 24 is obtained from commercially available 1,3-bis(3-mercaptopropyl) disiloxane 23 by reaction with 2-isocyanatoethyl methacrylate.

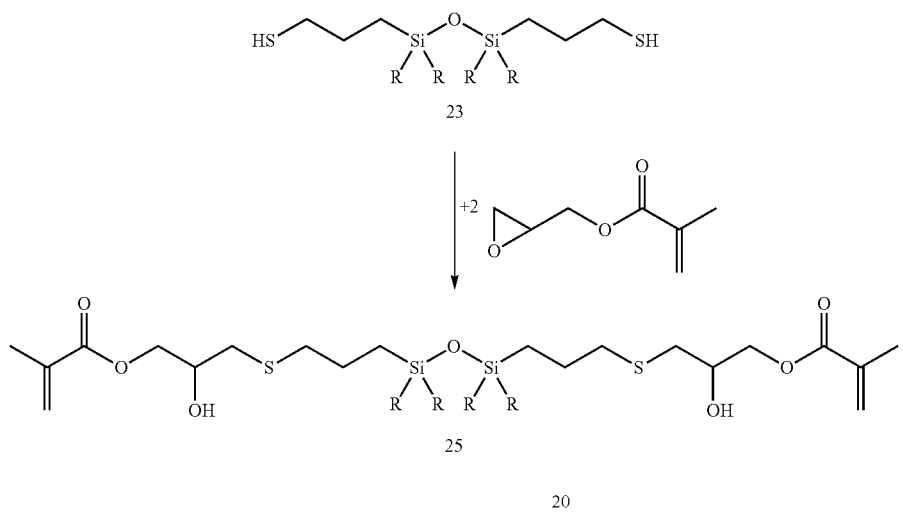
The corresponding disiloxane 25 is obtainable from 1,3-bis(3-mercaptopropyl)disiloxane 23 by reaction with glycidyl methacrylate.
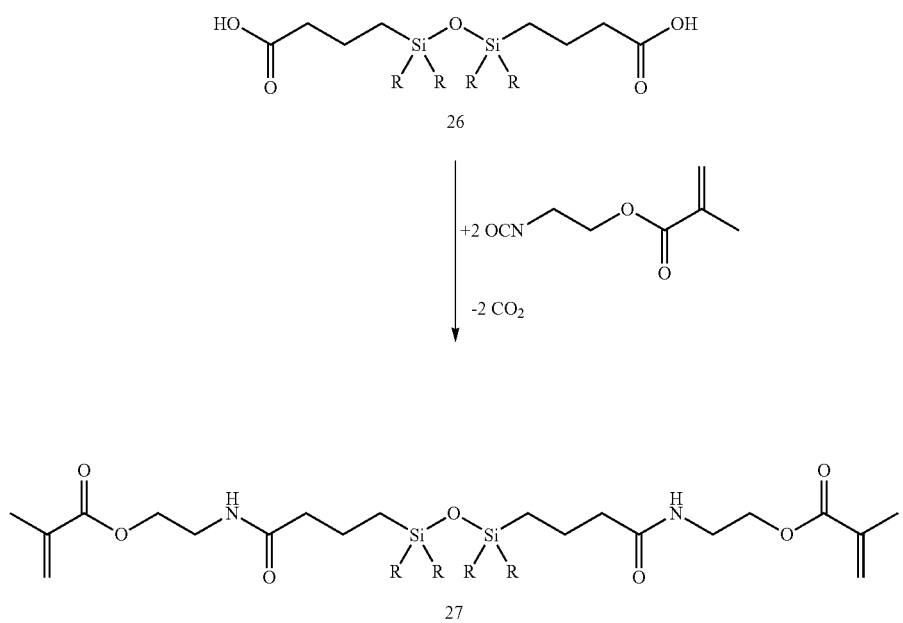
The corresponding amide derivative 27 is obtained from commercially available 1,3-bis(3-carboxypropyl)-disiloxane 26 by reaction with 2-isocyanatoethyl methacrylate.
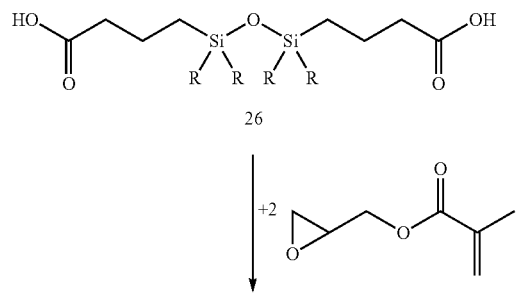

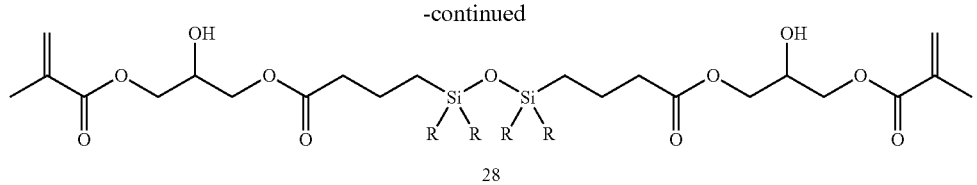

28

The corresponding disiloxane 28 is also obtainable from 1,3-bis(3-carboxypropyl)disiloxane 26 by reaction with glycidyl methacrylate.

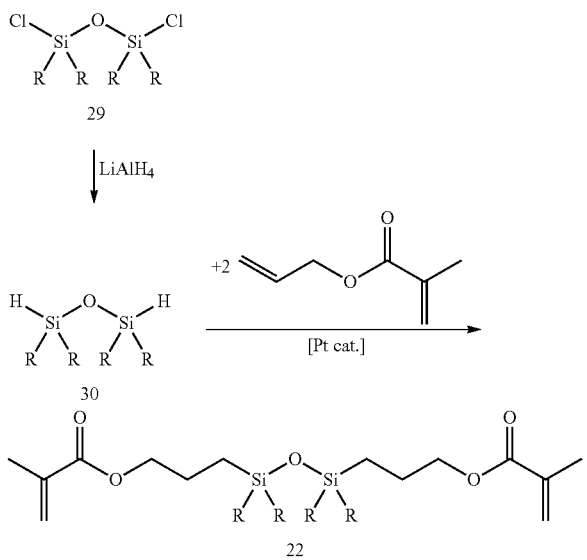

Of course, a multitude of (meth)acryloyl-substituted disiloxanes proceeding from the dichlorodisiloxanes are also obtainable via typical silane chemistry. Mention is made here by way of example of the reaction with lithium aluminum hydride to give the dihydrodisiloxane and subsequent platinum-catalyzed reaction with allyl methacrylate to give the corresponding 1,3-bis(3-methacryloyloxypropyl)disiloxane 22.

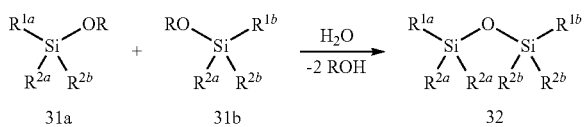

Of course, the inventive disiloxanes are not just obtainable by functionalization of disiloxanes, but can also be prepared proceeding from monoalkoxysilanes by hydrolysis and condensation. For example, the unsymmetric disiloxanes 32 are also obtainable by reaction of different monoalkoxysilanes 31a/b. For the functionalization of the monoalkoxysilanes, conceivable functionalization reactions include those already described for the disiloxanes.

Constituent c—optionally one, two, three or more free-radically curable monomers having no silicon atom The free-radically curable monomers having no Si atom are monomers which are substances having preferably one, two or more ethylenic groups, for example but not restricted to (meth)acrylate monomers.

The (meth)acrylate monomers may be monofunctional or else polyfunctional.

Monofunctional (meth)acrylate monomers used with preference are the esters of (meth)acrylic acid with alkyl groups of 1 to 12 carbon atoms and esters of (meth)acrylic acid containing aromatic groups having 6 to 12 carbon atoms, wherein the alkyl groups and aromatic groups that form the esters may contain substituents such as hydroxyl groups and ether bonds.

The patent literature mentions a multitude of further compounds (for example in DE 39 41 629 A1, which is incorporated in the present application by way of reference), all of which are esters of acrylic or methacrylic acid and are suitable for use in a curable mixture.

The free-radically polymerizable monomers may also be hydroxyl compounds having at least one ethylenic double bond. In this case, it is possible with preference to use the customarily used hydroxyl compounds of (meth)acrylates.

Examples of polyfunctional (meth)acrylate monomers also include di(meth)acrylates of alkylene glycol having 2 to 20 carbon atoms, di(meth)acrylates of oligomers of alkylene glycol, polyalkylene glycol di(meth)acrylate, di(meth)acrylates of bisphenol A or of the diglycidyl ether of bisphenol A.

Particular preference is further given to free-radically curable compounds based on a central polyalicyclic structural element, for example 3(4),8(9)-bis((meth)acryloyloxymethyl)tricyclo[5.2.1.0$^{2,6}$]decane, alkoxylated 3(4),8(9)-bis((meth)acryloyloxy-methyl)tricyclo[5.2.1.0$^{2,6}$] decane, 2,3-bis((meth)acryloyloxymethyl)bicyclo[2.2.1] heptane, alkoxylated 2,3-bis((meth)acryloyloxymethyl) bicyclo[2.2.1]heptane, 1,3,5-tri(meth)acryloyloxytricyclo [3.3.1.1$^{3,7}$]decane, alkoxylated tri(meth)acryloyloxytricyclo [3.3.1.1$^{3,7}$]-decane, and (meth)acrylates of tricyclo[5.2.1.0$^{2,6}$]-decane-3(4),8(9)-dimethanol, alkoxylated tricyclo-[5.2.1.0$^{2,6}$]decane-3(4),8(9)-dimethanol, bicyclo[2.2.1]-heptane-2,3-dimethanol, alkoxylated bicyclo[2.2.1]-heptane-2,3-dimethanol, 1,3,5-adamantanetriol, alkoxylated 1,3,5-adamantanetriol, with urethane, urea, amide, allophanate, acylurea or biuret groups arranged between the polyalicyclic structural element and the (meth)acrylates.

Details of the preparation of these substituted (meth) acrylates can be found in patent applications EP 11 183 333, EP 11 183 328, EP 11 183 345, EP 11 183 338, EP 11 183 342 and EP 11 188 086, and in the publications cited in these documents. These citations are likewise incorporated into the present application by way of reference.

Preference is likewise given to urethane (meth)acrylates, reaction products formed from 2 mol of a (meth)acrylate with a hydroxyl group and one mole of a diisocyanate.

In a preferred curable mixture of the invention, constituent (c) contains one or more (meth)acrylate monomers chosen from the group consisting of 3(4),8(9)-bis((meth) acryloyloxymethyl)tricyclo[5.2.1.0$^{2,6}$]decane, alkoxylated 3(4),8(9)-bis((meth)acryloyloxy-methyl)tricyclo[5.2.1.0$^{2,6}$] decane, 2,3-bis((meth)acryloyloxymethyl)bicyclo[2.2.1] heptane, alkoxylated 2,3-bis((meth)acryloyloxymethyl)bicyclo[2.2.1]heptane, 1,3,5-tri(meth)acryloyloxytricyclo[3.3.1.1$^{3,7}$]decane, alkoxylated tri(meth)acryloyloxytricyclo[3.3.1.1$^{3,7}$]-decane, (meth)acrylates of tricyclo[5.2.1.0$^{2,6}$]-decane-3(4),8(9)-dimethanol, alkoxylated tricyclo-[5.2.1.0$^{2,6}$]decane-3(4),8(9)-dimethanol, bicyclo[2.2.1]-heptane-2,3-dimethanol, alkoxylated bicyclo[2.2.1]-heptane-2,3-dimethanol, 1,3,5-adamantanetriol, alkoxylated 1,3,5-adamantanetriol, with urethane, urea, amide, allophanate, acylurea or biuret groups arranged between the polyalicyclic structural element and the (meth)acrylates, ethylene glycol di(meth)acrylate, hexane-1,6-diol di(meth)acrylate (HEDMA), triethylene glycol di(meth)acrylate (TEGDMA), dodecane-1,12-diol di(meth)acrylate, bisphenol A di(meth)acrylate, alkoxylated bisphenol A di(meth)acrylate, bisphenol B di(meth)acrylate, alkoxylated bisphenol B di(meth)acrylate, bisphenol C di(meth)acrylate, alkoxylated bisphenol C di(meth)acrylate, bisphenol F di(meth)acrylate, alkoxylated bisphenol F di(meth)acrylate, polyethylene glycol di(meth)acrylate, 7,7,9-trimethyl-4,13-dioxo-5,12-diazahexadecane 1,16-dioxydi(meth)acrylate (UDMA), butanediol di(meth)acrylate, tetraethylene glycol di(meth)acrylate, neopentyl glycol di(meth)acrylate, 2-hydroxypropyl-1,3-di(meth)acrylate, 3-hydroxypropy-1,2-di(meth)acrylate, pentaerythritol di(meth)acrylate, di(meth)acrylates of dihydroxymethyl-tricyclo-[5.2.1.0$^{2,6}$]decane, 2-hydroxyethyl(meth)acrylate, 2-hydroxypropyl(meth)acrylate, 3-hydroxypropyl(meth)-acrylate, 1,2-dihydroxypropyl(meth)acrylate, 1,3-dihydroxypropyl(meth)acrylate, 2,2-bis[4-(3-(meth)-acryloyloxy-2-hydroxypropoxy)phenyl]propane (bis-GMA), trimethylolpropane tri(meth)acrylate, trimethylolethane tri(meth)acrylate, pentaerythritol tri(meth)acrylate, trimethylolmethane tri(meth)acrylate, pentaerythritoltetra(meth)acrylate, dimethylolpropanetetra(meth)-acrylate, pentaerythritol-hexa(meth)acrylate, butylene glycol di(meth)acrylate, propylene glycol di(meth)acrylate, nonanediodi(meth)acrylate, decane-diol di(meth)acrylate, glycerol mono(meth)acrylate, glycerol di(meth)acrylate, trimethylolpropane mono(meth)acrylate, trimethylolpropane di(meth)-acrylate, sorbitol mono-, di-, tri-, tetra- or penta(meth)acrylate, methyl(meth)acrylate, ethyl (meth)acrylate, propyl(meth)acrylate, butyl (meth)acrylate, hexyl (meth)acrylate, tetrahydrofurfuryl (meth)acrylate, lauryl (meth)acrylate, cyclohexyl (meth)acrylate, allyl (meth)acrylate, glycidyl (meth)acrylate, 2-ethoxyethyl(meth)acrylate, methoxy-polyethylene glycol(meth)acrylate, isobornyl (meth)-acrylate, 2-(N,N-dimethylamino)ethyl (meth)acrylate, N-methylol(meth)acrylamide, diacetone(meth)acrylamide, 2,2-bis[4-(meth)acryloyloxyphenyl]propane, 2,2-bis[4-(meth)acryloyloxyethoxyphenyl]propane, 2,2-bis[4-(meth)acryloyloxydiethoxyphenyl]propane, 2,2-bis[4-(meth)acryloyloxytriethoxyphenyl]propane, 2,2-bis[4-(meth)acryloyloxytetraethoxyphenyl]propane, 2,2-bis[4-(meth)acryloyloxypentaethoxyphenyl]propane, 2,2-bis[4-(meth)acryloyloxydipropoxyphenyl]propane, 2-[4-(meth)acryloyloxyethoxyphenyl]-2-[4-(meth)acryloyloxydiethoxyphenyl]propane, 2-[4-(meth)acryloyloxydiethoxyphenyl]-2-[4-(meth)acryloyloxytriethoxyphenyl]propane, 2-[4-(meth)acryloyloxydipropoxyphenyl]-2-[4-(meth)acryloyloxytriethoxyphenyl]propane, 2,2-bis[4-(meth)acryloyloxyisopropoxyphenyl]propane, neopentylglycolhydroxypivalatedi(meth)acrylate, acetoacetatoxyethyl (meth)acrylate, polypropyleneglycol di(meth)acrylate, glycerolalkoxylateddimethacrylate, neopentyl glycol (meth)acrylate, N,N-(1,2-dihydroxyethylene) bisacrylamide, 2,2-bis[4-(meth)acryloyloxypentaethoxyphenyl]propane, 2,2-bis[4-(meth)acryloyloxypolyethoxyphenyl]propane, diethylene glycol di(meth)acrylate, dipentaerythritol tetra(meth)acrylate, dipentaerythritolhexa(meth)-acrylate, N,N-(2,2,4-trimethylhexamethylene)bis[2-(aminocarboxy)-propane-1,3-diol] tetra(meth)acrylate, the condensation product of 3-(4)(meth)acryloyloxy methyl-8(9)-hydroxymethyltricyclo[5.2.1.0$^{2,6}$]decane with dicarboxylic acids, 2-ethylhexyl(meth)acrylate, tridecyl (meth)acrylate, stearyl(meth)acrylate, benzyl (meth)acrylate, methoxy diethylene glycol (meth)acrylate, dicyclopentenyl (meth)acrylate, phenyl (meth)acrylate, pentaerythritol mono(meth)acrylate, dipentaerythritol mono(meth)acrylate, caprolactone-modified tetrahydrofurfuryl (meth)acrylate.

Constituent d—fillers

A free-radically curable dental composition of the invention contains a proportion of filler particles of 85% by weight or less, preferably of 78% by weight or less, based on the total mass of the dental composition of the invention.

As constituent (d), it is possible to use organic and/or inorganic fillers.

Organic filler particles comprise or consist of, for example, one or more compounds selected from the group consisting of polyvinyl acetate and copolymers of polyvinyl acetate with one or more polymerizable compounds, polystyrene, polyethylene, polypropylene, waxes such as polyethylene wax, polybutylene, polybutadiene, copolymers of butadiene and styrene, polyacrylonitrile, resins such as rosin or hydrocarbon resins, poly(meth)acrylate esters, i.e. reaction products of poly(meth)acrylic acid with linear or branched aliphatic, aromatic or cycloaliphatic alcohols such as methanol, ethanol, propanol, isopropanol, the isomeric butanols and higher homologs of the alcohols mentioned having up to 22 carbon atoms, cyclohexanol, benzyl alcohol and the like, polydialkyl maleates such as dibutyl maleate and copolymers thereof, and polymers containing silyl groups, such as polyvinylsilanes or copolymers of vinylsilane with one or more of the monomers mentioned. The organic fillers can be used alone or as mixtures.

The inorganic fillers can likewise be used alone or as mixtures. To optimize the product properties, the inorganic fillers can be introduced into the formulations in different particle sizes. The fillers may have a unimodal or polymodal distribution, for example a bimodal distribution.

As inorganic fillers, it is possible to use compact glasses and different silicas in various sizes and states (monodisperse, polydisperse).

Suitable inorganic constituents are, for example, amorphous materials based on mixed oxides composed of $SiO_2$, $ZrO_2$ and/or $TiO_2$, and also fillers such as quartz glass ceramic or glass powders, barium silicate glasses, barium fluorosilicate glasses, strontium silicate glasses, strontium borosilicate, Li/Al silicate glasses, barium glasses, calcium silicates, sodium aluminosilicates, fluoroaluminosilicate glasses, oxides of aluminum or silicon, zeolites, apatite, zirconium silicates, sparingly soluble metal salts such as barium sulfate or calcium chloride, and x-ray-opaque fillers such as ytterbium fluoride.

For better incorporation into the polymer matrix, the fillers may be organically surface-modified. One example is the surface treatment of the fillers with a silane. A particularly suitable adhesion promoter is methacryloyloxypropyltrimethoxysilane.

To adjust the rheology, the free-radically curable compositions may contain different silicas, preferably fumed silicas.

Preferably, the curable compositions of the invention contain nanoscale solid particles. The nanoscale solid particles are particles having an average particle size of not more than 200 nm, preferably not more than 100 nm and especially not more than 70 nm. The nanoscale inorganic solid particles are preferably those of oxides, sulfides, selenides and tellurides of metals, semimetals and mixtures thereof. Particular preference is given to nanoscale particles of $SiO_2$, $TiO_2$, $ZrO_2$, ZnO, $SnO_2$ and $Al_2O_3$, and mixtures thereof. The nanoscale solid particles are produced in a known manner, for example by flame pyrolysis, plasma methods, gas phase condensation, colloid techniques, precipitation methods, sol-gel methods, etc.

In a preferred configuration, the nanoscale particles are in nonagglomerated and/or nonaggregated form, for example dispersed in a medium, preferably in monodisperse form.

In order to enable good binding of the nanoparticles into the polymer matrix of a free-radically curable dental composition of the invention, the surfaces of the nanoparticles have likewise been organically surface-modified, meaning that their surfaces have organic structural elements. Examples include the surface treatment of the fillers with a silane. A particularly suitable adhesion promoter here too is methacryloyloxypropyltrimethoxysilane.

In a further preferred configuration, the nanoscale particles are thus nonagglomerated and/or nonaggregated, organically surface-modified nanoparticles having an average particle size of less than 200 nm, preferably less than 100 nm, more preferably less than 70 nm, which have in turn preferably been silanized.

Commercially available nanoscale, nonagglomerated and nonaggregated silica sols which can be used in accordance with the invention are traded for example, under the "NALCO COLLOIDAL SILICAS" (Nalco Chemical Co.), "Ludox colloidal silica" (Grace) or "Highlink OG" (Clariant) names.

In a preferred configuration, the filler fraction of a free-radically curable composition of the invention comprises a mixture of a first filler (d1) in the form of nonagglomerated, nonaggregated organically surface-modified nanoparticles having an average particle size of less than 200 nm and a second filler (d2) in the form of microparticles having an average particle size in the range from 0.4 µm to 10 µm. The combination of (d1) nanoparticles and (d2) microparticles in a free-radically curable composition of the invention achieves complete and homogeneous filling of volume of the composite material. This reduces both the shrinkage of the free-radically curable composition in the course of curing of the polymer matrix and the susceptibility of the composition of the invention to abrasion.

The proportion of organically surface-modified nanoparticles in a preferred free-radically curable composition of the invention having an average particle size of less than 200 nm is greater than 1% by weight, preferably greater than 2% by weight and more preferably greater than 3% by weight. In in-house studies, it has been found that, in the case of a content of 1% by weight or less of nonagglomerated and/or nonaggregated organically surface-modified nanoparticles having an average particle size of less than 200 nm, the free-radically curable composition no longer has a sufficient abrasion resistance in each individual case. One reason for this is probably that, in the case of a content of 1% by weight or less of said nanoparticles, the cavities between the microparticles having an average particle size of 0.4 µm to 10 µm are no longer filled adequately. On the other hand, it has been shown that, in the case of a content of more than 50% by weight of nonagglomerated and/or -aggregated, organically surface-modified nanoparticles having an average particle size of less than 200 nm, processibility of the composition is no longer adequate. Because of the high solids content, its viscosity then becomes too high.

The materials for the nanoparticles for use in accordance with the invention are preferably oxides or mixed oxides and are preferably selected from the group consisting of oxides and mixed oxides of the elements silicon, titanium, yttrium, strontium, barium, zirconium, hafnium, niobium, tantalum, tungsten, bismuth, molybdenum, tin, zinc, ytterbium, lanthanum, cerium, aluminum and mixtures thereof. The preferred oxidic nanoparticles are, as explained, nonagglomerated and/or nonaggregated, and have been organically surface-treated.

Within a free-radically curable composition of the invention, the microparticles bring about substantially homogeneous filling of volume, with the remaining cavities between the microparticles at least partly filled by the above-described nanoparticles (component (d1)). In connection with the present invention, microparticles are understood to mean particles having an average particle size of 400 nm to 10 µm. Preferably, the average particle size is less than 5 µm. It has been found that the completeness and homogeneity of the filling of volume by the free-radically curable composition which is already achievable with the microparticles increases with decreasing microparticle size.

The microparticles of component (d2) may have a monomodal or polymodal particle size distribution, for example a bimodal particle size distribution. Microparticles having a bimodal or multimodal particle size distribution are preferable in accordance with the invention, since more complete filling of volume is achievable therewith than in the case of general use of microparticles having monomodal particle size distribution. In the presence of a bi- or multimodal particle size distribution, the particles of the fractions having the larger particle size bring about coarse filling of volume, while the particles of the fraction having the smaller particle size, as far as possible, fill the cavities between the particles of the fractions having the larger particle size. The cavities still remaining are filled by nanoparticles as described above.

Most preferably, therefore, in a free-radically curable composition of the invention, a component (d2) containing two or more fractions of microparticles, with different average particle sizes of the fractions, is used.

Preferably, component (d2) contains at least two microparticle fractions wherein the average particle sizes differ from one another by at least 0.5 µm, preferably by at least 0.7 µm. In some configurations, the difference between the average particle sizes of the microparticle fractions is at least 1.0 µm.

The microparticles of different fractions may consist of the same material or of different materials; it is also possible for there to be two or more fractions of microparticles having average particle sizes that are approximately the same or within a particular range, in which case the materials of the particles differ between the fractions.

More preferably, a free-radically curable composition of the invention comprises a component (d2) having one or more first microparticle fractions each having an average particle size in the range from 1 µm to 10 µm, preferably 1 µm to 5 µm, and one or more second microparticle fractions each having an average particle size in the range from >0.4 µm to <1 µm (i.e. larger than 0.4 µm but smaller than 1 µm), preferably 0.5 µm to 0.8 µm.

Preferably, the ratio of the total mass of the first microparticle fractions to the total mass of the second microparticle fractions is in the range from 1:1 to 12:1, preferably in the range from 1.5:1 to 8:1.

Preferably, the ratio of the average particle size of the or a first microparticle fraction to the average particle size of the or a second microparticle fraction of component (d2) is in the range from 1.5:1 to 10:1, preferably in the range from 2:1 to 5:1.

In a particularly preferred free-radically curable composition of the invention, component (d2) comprises one or more first microparticle fractions each having an average particle size in the range from 1 μm to 10 μm, preferably 1 μm to 5 μm, and one or more second microparticle fractions each having an average particle size in the range from >0.4 μm to <1 μm, preferably 0.5 μm to 0.8 μm; wherein the ratio of the total mass of the first microparticle fractions to the total mass of the second microparticle fractions is in the range from 1:1 to 12:1, preferably 1.5:1 to 8:1 and/or the ratio of the average particle size of the or a first microparticle fraction to the average particle size of the or a second microparticle fraction of component (d2) is in the range from 1.5:1 to 10:1, preferably 2:1 to 5:1.

In a particularly preferred free-radically curable composition of the invention, at least a portion of the microparticles of component (d2) is formed by organically surface-modified particles, preferably silanized particles, and/or at least a portion of the microparticles of component (d2) is formed by glass particles; preferably, at least a portion of the microparticles of component (d2) is formed by organically surface-modified glass particles, preferably silanized glass particles.

In these cases, component (d2) preferably features a bi- or multimodal particle size distribution, especially a bi- or multimodal particle size distribution having the preferred features described above.

As well as components (d1) and (d2), the free-radically curable composition may comprise further fillers as component (d3) in addition to the mixture of filler particles.

For example, it is possible to use reinforcing filler materials such as glass fibers, polyamide fibers or carbon fibers. A free-radically curable composition of the invention may also contain fine splinter or bead polymers, wherein the bead polymers may be homo- or copolymers of organically curable monomers.

In a particularly preferred embodiment, in the case that moldings are planned for the medical sector, especially the dental sector, by an additive manufacturing method, a free-radically curable composition of the invention contains an x-ray-opaque filler. Most preferably, the composition of the invention contains nanoscale $YbF_3$ and/or $BaSO_4$.

Qualitative and Quantitative Characterization of the Filler Particles:

The steps described hereinafter in the qualitative and quantitative characterization of the filler particles (especially of nanoscale filler particles) are well known to those skilled in the art and are described comprehensively in the literature.

Resin/Filler Separation:

In a first step, 1 g of a free-radically curable composition of the invention (also called composite material hereinafter) is resuspended in 10 mL of acetone and the resultant suspension is then centrifuged with a centrifuge at 5000 rpm for 10 min. The supernatant (called resin phase hereinafter) is decanted off into a collection bottle and the residue is slurried in 5 mL of acetone. The mixture is centrifuged again at 5000 rpm for 10 min and decanted, and the residue is slurried again in 5 mL of acetone. The steps of centrifuge, decanting and slurrying are repeated twice more under identical conditions. The total amount of residues separated from the resin phases is dried, and the total amount of resin phases is freed of acetone on a rotary evaporator.

After conducting the first step, the dried total amount of residues regularly includes those filler particles having a particle size of about 400 nm or greater than 400 nm (called macroscopic filler particles hereinafter). The total amount of resin phases freed of acetone (called resin fraction hereinafter) regularly also includes, as well as polymerizable monomers, filler particles having a particle size of about 400 nm or especially less than 400 nm (called nanoscale particles hereinafter). This method therefore ensures that the composite material, by centrifugation, is separated completely into (i) a fraction of macroscopic filler particles, especially with regard to the glasses having a size in the order of magnitude of greater than 400 nm up to the high micrometer range, and (ii) a resin fraction including nanoscale particles.

The median particle size $d_{50}$ of the macroscopic filler particles for use in accordance with the invention in the filler component (d2) of a composition of the invention is determined by means of light scattering (laser diffraction), preferably with a Beckman Coulter LS 13320 particle size analyzer.

The nanoscale particles present in the resin fraction may, for example, be both nonaggregated and/or nonagglomerated particles, for example including x-ray-opaque particles, for example $YbF_3$ or $BaSO_4$, having particle sizes within a range from about 3 nm to 200 nm, preferably from 5 nm to 200 nm, more preferably from 7 nm to 100 nm and most preferably from 7 nm to 70 nm, and non-x-ray-opaque silicas which take the form, for example, of fumed silicas in the form of aggregates and/or agglomerates having a particle size within a range from about 150 nm to about 300 nm, or else silicas which are synthesized by the sol-gel process (or else from waterglass) and which are likewise in nonaggregated and/or nonagglomerated form and have particle sizes within a range from about 3 nm to 200 nm, preferably from 5 nm to 200 nm, more preferably from 7 nm to 100 mm and most preferably from 7 nm to 70 nm.

The total proportion by mass of inorganic particles in the resin fraction is determined gravimetrically by difference weighing after asking of an appropriate resin fraction.

TEM in Combination with EELS:

In a second step, the filler particles in the resin fraction are subjected to a qualitative and quantitative characterization. For this purpose, TEM (transmission electron microscopy) is used in conjunction with EELS (electron energy loss spectroscopy).

By means of TEM, the particle sizes of the individual particles and the number thereof are determined; elemental determination of individual particles is effected by means of EELS.

To conduct the combined TEM/EELS characterization, in a first step, the concentration of the nanoscale particles in the resin fraction is first reduced by dilution with curable resin. This very substantially rules out observation of "overlapping" of nanoscale particles in the later images. Such "overlapping" would distort the particle characterization. In-house studies have shown that the optimal particle concentration (i.e. the proportion by volume of the filler particles) for such studies is 1% by volume, based on the total mass of the diluted sample.

In a second step, bar specimens are produced by curing the diluted resin fractions obtained by dilution with curable resin. These bar specimens are then used to produce several ultrathin sections of thickness 300 nm with an ultra-diamond knife (for example ULTRACUT UCT, LEICA, Wetzlar). The ultrathin sections are transferred to copper TEM grids for stabilization. This results in thin section preparations.

These thin section preparations are then analyzed with acceleration voltage 120 kV in a TEM with bright field images.

A TEM analysis of the above-described thin section preparations allows distinction of nonaggregated and nonagglomerated nanoscale particles from aggregated and/or agglomerated particles (e.g. silicas, for example Aerosils) (for identification of the chemical composition see the details which follow).

If high-resolution images are to be examined, ultrathin sections having layer thicknesses of less than 100 nm can be produced and examined.

In a third step, the filler particles in the ultrathin sections or thin section preparations are chemically characterized by means of EELS point analyses, such that the chemical composition of individual particles becomes known (for determination of the surface modification of particles see the points below).

The volume- or weight-based proportions of particle fractions (including a plurality thereof if appropriate) are determined in a fourth step from a TEM image as follows: the image section from a TEM image viewed under a microscope is an area having edge lengths a and b which can be determined by means of the legend. Multiplying by the thickness c of the ultrathin section gives a total volume $V_{total}$ for the area under consideration in the TEM. This total volume $V_{total}$ is the sum total of the resin volume $V_{resin}$ and the volume of all the particles $V_{particles}$ within this volume (the volume of all the particles may include several groups of particles, for example sorted by various criteria, for example size). The following equation holds:

$$V_{total} = a*b*c = V_{resin} + V_{particles}.$$

The volume of individual particles (and hence the volume of all the particles in the volume under consideration) can be obtained by calculation via the sphere volume of the individual particles. For this purpose, in the TEM image, the diameter or radius of an appropriate particle is determined. The sphere volume calculated therefrom, multiplied by the density of the corresponding material of which the particle consists (material identifiable by means of EELS), gives the mass of the particle. The resin volume, obtainable from the total volume minus the particle volume, multiplied by the resin density, gives the resin mass. The resin density is obtained very substantially from the density of the resin used for dilution and, if appropriate, the density of the diluted resin fraction (the latter can possibly be neglected in the calculation of the resin density if the proportion of the diluted resin is negligible). The proportion of the particles (or a group of particles) in percent by weight is calculated from $m_p*100/(m_{particles}+m_{resin})$ where $m_p$ is the mass of the particle fraction under consideration in the volume under consideration, $m_{particles}$ is the mass of all the particles in the volume in question and $m_{resin}$ is the mass of the resin in the volume under consideration. In the final calculation of the proportion by weight of the particle fraction under consideration, the dilution factor is taken into account appropriately.

Determination of Organic Surface Modifications:
Preliminary Assessment:

Many known x-ray-opaque filler materials (for example ytterbium fluoride or barium sulfate) have the disadvantage that they can be incorporated only with difficulty into the matrix (resin matrix) composed of polymerizable monomers (called the organic resin phase) because they do not enter into sufficient chemical bonds (binding options) with the hydrophobic groups of the medium. Vitreous fillers can be incorporated in an excellent manner into the resin matrix of dental composite materials, for example, with the aid of silanization via Si—OH groups. In the case of ytterbium fluoride and barium sulfate, no such groups are present on the surfaces; they are therefore not silanizable and lead to inadequate physical and chemical resistance in a cured dental material (see WO 2005/011621 A1, bottom of page 2).

The x-ray-opaque nanoscale particles used in a curable material of the invention therefore will not have any silanes on their surfaces. Instead, the linking is effected via nitrogen, oxygen, sulfur and/or phosphorus atoms (again see WO 2005/011621 A1 and our remarks further up in the text).

Removal of Polymerizable Monomers from Nanoscale Particles:
"Cross-Flow" Method:

The removal of polymerizable monomers from nanoscale particles is effected, for example, in a "cross-flow" method known to those skilled in the art by means of ultrafiltration membranes.

In this method, a resin fraction comprising nanoscale particles, polymerizable monomers and optionally a suitable diluent is pumped from a vessel by means of a pump into a circuit composed of particular membranes, and the polymerizable monomers pass through the pores of the membranes and are separated as filtrate, while the nanoscale particles remain within the circuit (and hence within the vessel).

An example of a suitable system for this separating step is the "Vivaflow 50" system from "Sartorius Stedim Biotech GmbH, Göttingen". The pump drive (7554-95) and pump head come from the "Masterflex L/S" series from "Cole-Parmer Instrument Co.", Illinois, USA. The operation of the pump is set to 2.5 bar during the filtration. Two separation membranes of the "50,000 MWCO (PES)" type are connected in series. The MWCO (molecular weight cutoff) defines the separation limit here, i.e. the size of the molecules which can still pass efficiently through the membrane. This value is reported in daltons. The fractions obtained are subsequently analyzed as described below.

Sedimentation Field-Flow Fractionation (SF3):

Even better than the "cross-flow" method is the conduction of a sedimentation field-flow fractionation (SF3). This can especially separate different particle fractions from one another and additionally from the resin fraction. It is a prerequisite here that the different particle fractions differ sufficiently from one another in terms of size and/or density.

Corresponding equipment containing a separation column necessary for the purpose is obtainable from Postnova Analytics GmbH, Landsberg. The module containing the separation column is identified as CF2000 Centrifugal FFF and is supplemented by the further modules PN7140 (Eluent Organizer), PN1130 (Isocratic Pump), PN5300 (Autosampler), PN3621 MALS (21-Multi-Angle Light Scattering Detector) and PN8050 (Fraction Collector). In this combination, the Centrifugal FFF system allows not just the analytical but also the preparative separation of particle fractions. The fractions obtained are subsequently analyzed as described below.

Characterization of the Surface Modification:

A sample which has been produced as above and then freed of solvents, containing nanoscale particles in the form of a powder, is subsequently examined by means of spectroscopic methods (for example by means of 1H NMR, 13C NMR, 15N NMR, 29Si NMR and 31P NMR, and also IR).

Signals which cannot be attributed to a silane, for example the gamma-methacryloyloxypropylsilyl radical, are attributed to organic surface modifications not based on silanes, for example surface modifications by means of organic compounds on surfaces of ytterbium fluoride or barium sulfate particles.

The proportions of organically surface-modified particles and/or non-organically surface-modified particles can also be determined regularly by evaluation of the intensities of corresponding vibration bands in the IR spectrum. For this purpose, reference vibration bands (reference curves) of organically surface-modified or non-organically surface-modified particles with the corresponding chemical compositions are employed.

Characterization by Means of Image Analysis and Raman Spectroscopy:

The person skilled in the art is aware of additional methods and coupled methods which allow qualitative and quantitative characterization of the filler particles. In this respect, reference is made, for example, to the article "Chemische Identität einzelner Partikel" [Chemical Identity of Individual Particles] by Deborah Huck-Jones and Renate Hessemann in "Nachrichten aus der Chemie", Volume 62, September 2014, pages 886 and 887. The combination of image analysis and Raman spectroscopy disclosed therein is regularly also suitable for characterization of the filler particles in the context of the present invention. This is especially true of samples which are obtained by the resin/filler separation described above. An example of a suitable image analysis is again the TEM analysis described in the text above.

Constituent e—initiators and/or catalysts for the free-radical polymerization

A free-radically curable composition of the invention is preferably light-curable and/or chemically curable. Preference is given to a free-radically curable dental composition of the invention, wherein constituent (e) comprises or consists of one or more light-curing initiators and/or one or more initiators for chemical curing.

Preferred free-radically curable compositions of the invention are light-curable (photocurable) and comprise light-curing initiators. Examples of a light-curing initiator include substances having only photosensitizing action and combinations of sensitizer and accelerator.

Examples of photosensitizers are alpha-diketones, benzoin alkyl ethers, thioxanthones, benzophenones, acylphosphine oxides, bisacylphosphine oxides, acylgermanium compounds, acetophenones, ketals, titanocenes, sensitizing dyes, etc. The sensitizers can be employed alone or in combination. Specific substance examples from different classes can be found, for example, in DE 10 2006 019 092 A1, or in DE 39 41 629 C2, which are incorporated into the present application by way of reference.

Examples of accelerators which are used together with the sensitizers are tertiary amines, secondary amines, barbiturate acids, tin compounds, aldehydes and sulfur compounds. Specific substance examples from different classes can be found, for example, in DE 10 2006 019 092 A1 or in DE 39 41 629 C2, which are incorporated into the present application by way of reference.

Further suitable initiators and initiator combinations are described in DE 601 16 142, which is incorporated into the present application by way of reference.

The absorption maximum of camphorquinone (CQ) is about 470 nm and is therefore within the blue light range. Camphorquinone (CQ) is one of the $PI_2$ initiators and is regularly used together with a coinitiator.

Preferably, a composition of the invention contains the combination of an alpha-diketone and an aromatic tertiary amine, preference being given to the combination of camphorquinone (CQ) and ethyl p-N,N-dimethylaminobenzoate (DABE).

Likewise preferable is the further combination of the "alpha-diketone/aromatic tertiary amine" system with a phosphine oxide, especially with phenyl bis(2,4,6-trimethylbenzoyl)phosphine oxide and/or 2,4,6-trimethylbenzoyldiphenylphosphine oxide. With regard to the structures of suitable phosphine oxides for use in a free-radically curable composition of the invention, reference is made to publications DE 38 01 511 C2, DE 10 2006 050 153 A1, EP 0 184 095 B1, DE 42 31 579 C2, EP 0 366 977 B1, U.S. Pat. No. 7,081,485 B2, DE 32 36 026 A1, US 2007/0027229 A1, EP 0 262 629 B1, EP 0 073 413, U.S. Pat. No. 7,148,382 B2, U.S. Pat. No. 5,761,169, DE 197 08 294 A1, EP 0 057 474, EP 0 047 902 A, EP 0 007 508, DE 600 29 481 T2, EP 0 980 682 B1, EP 0 948 955 B1, EP 1 236 459 B1 and EP 0 173 567 A2, which are incorporated into the present application by way of reference.

The phosphine oxides specified in these publications are suitable especially alone or in combination with the "alpha-diketone/amine" system as photo-polymerization initiator system in a free-radically curable composition of the invention.

EP 1 905 415 describes polymerizable dental compositions comprising acylgermanium compounds as initiators.

Alternatively, it is also possible to use borate salts, as described, for example, in U.S. Pat. Nos. 4,772,530, 4,954, 414, 4,874,450, 5,055,372 and 5,057,393, as photoinitiators, which are incorporated into the present application by way of reference.

Further suitable photoinitiators are described in J.-P. Fouassier, Photoinitiation, Photopolymerization and Photocuring, Hanser Publishers, Munich, Vienna, N.Y. 1995, and in J. F. Rabek (ed.), Radiation Curing in Polymer Science and Technology, Vol. II, Elsevier Applied Science, London, N.Y. 1993, which are incorporated into the present application by way of reference.

Constituent f—further customary additives

A free-radically curable dental composition of the invention comprises one or more further additive(s) in some cases.

These additives may have various functions. Customary additives for use in dental materials are known to those skilled in the art; he or she will select the suitable additive(s) according to the desired function. Typical additives and their functions are described by way of example hereinafter.

Free-radically light-curable compositions as preferred in accordance with the invention preferably contain one or more inhibitor(s), also called stabilizer(s). These are typically added in order to prevent spontaneous polymerization. They react with free radicals formed prematurely, which are scavenged, prevent premature polymerization and increase the storage stability of the light-curable dental composition. Standard inhibitors are phenol derivatives such as hydroquinone monomethyl ether (HQME) or 2,6-di-tert-butyl-4-methylphenol (BHT). Further inhibitors such as tert-butylhydroxyanisole (BHA), 2,2-diphenyl-1-picrylhydrazyl radicals, galvinoxyl radicals, triphenylmethyl radicals, 2,3,6,6-tetramethylpiperidinyl-1-oxyl radicals (TEMPO), and derivatives of TEMPO or phenothiazine and derivatives of this compound are described in EP 0 783 880 B1, which is incorporated into the present application by way of reference. Alternative inhibitors are specified in DE 101 19 831 A1 or in EP 1 563 821 A1, which are incorporated into the present application by way of reference.

A free-radically curable composition preferred in accordance with the invention thus comprises, as additive, one or more polymerization inhibitors for increasing the storage stability of the composition, preferably selected from the group consisting of hydroquinone monomethyl ether (HQME), phenols, preferably 2,6-di-tert-butyl-4-methylphenol (BHT) and tert-butylhydroxyanisole (BHA), 2,2-diphenyl-1-picrylhydrazyl radicals, galvinoxyl radicals, triphenylmethyl radicals, 2,3,6,6-tetramethylpiperidinyl-1-oxyl radical (TEMPO) and derivatives thereof, and phenothiazine and derivatives thereof.

UV absorbers which are capable of absorbing UV radiation, for example, by their conjugated double bond systems and aromatic rings are in some cases part of a free-radically curable dental composition of the invention. Suitable absorbers are especially benzotriazoles, triazines, benzophenones, cyanoacrylates, salicylic acid derivatives, hindered amine light stabilizers (HALS) and mixtures thereof. Examples of UV absorbers are 2-hydroxy-4-methoxy-benzophenone, phenyl salicylate, 3-(2'-hydroxy-5'-methylphenyl)benzotriazole or diethyl 2,5-dihydroxy-terephthalate. Further absorbers are known to the expert from WO 2013/153183 A2, which is incorporated into the present application by way of reference.

Further optional additives are aromas, pigments, organic dyes, organic polymers and oligomers, preferably plasticizers, microbicides, preferably bactericides, interface-active substances, preferably surfactants, preservatives or molecular weight regulators.

In a preferred inventive use, the composition comprises the components in the following contents:
  a. 10%-70% by weight, preferably 10%-35% by weight,
  b. 2%-40% by weight, preferably 2%-25% by weight,
  c. 0%-30% by weight, preferably 0%-20% by weight,
  d. 0%-85% by weight, preferably 40%-78% by weight,
  e. 0.001%-5% by weight, preferably 0.1%-2% by weight and
  f. 0.001%-20% by weight, preferably 0.001%-10% by weight,
wherein the respective percentages by weight are based on the total mass of the composition.

In particularly preferred inventive uses, the free-radically curable composition does not contain any constituent c.

In particularly preferred inventive uses, a free-radically curable composition comprises 1,3-bis(3-methacryloyloxy-propyl)tetramethyldisiloxane as constituent b.

In a very particularly preferred inventive use, a free-radically curable composition does not contain any constituent c and contains 1,3-bis(3-methacryloyloxy-propyl)tetramethyldisiloxane as constituent b.

In a preferred inventive use, the additive manufacturing method comprises stereolithography, digital light processing, polyjet technology, 3D plotting, the galvanometer-type scanning method, micro-stereolithography, multijet modeling, selective laser sintering, 3D printing, fused deposition modeling, laminated object manufacturing or film transfer imaging.

In a particularly preferred inventive use, the additive manufacturing method comprises stereolithography, digital light processing and polyjet technology.

In a very particularly preferred inventive use, the additive manufacturing method comprises stereolithography.

In a particularly preferred inventive use, a dental molding is produced.

In a very particularly preferred inventive use, the dental molding is an inlay, an onlay, a veneer, a crown, a bridge, an artificial tooth, a denture, a scaffold, a temporary prosthesis, a partial or full prosthesis or else an orthodontic product.

The present invention also relates to a process for producing a molding, preferably a dental molding, in which a free-radically curable composition as defined above is cured layer by layer by introduction of radiation to form a three-dimensional body.

EXAMPLES

Substances used:
Polysiloxane I: Methacryl-POSS (MA0735, Hybrid Plastics Inc.)
Polysiloxane II: condensation product of 3-methacryloyloxypropyldimethoxy-methylsilane
Polysiloxane III: condensation product of 3-methacryloyloxypropyltrimethoxy-silane
Polysiloxane IV: condensation product of 3-[(2-hydroxy-3-methacryloyloxy)propoxy]propyldimethoxymethylsilane
Disiloxane I: 1,3-bis(3-methacryloyloxy-propyl)tetramethyldisiloxane
Disiloxane II: 1,3-bis[3-[(2-hydroxy-3-meth-acryloyloxy)propoxy]propyl]tetra-methyldisiloxane
Bis-GMA: 2,2-bis[4-(2-hydroxy-3-methacryloyloxy-propoxy)phenyl]propane
UDMA: 7,7,9-trimethyl-4,13-dioxo-5,12-diazahexadecane 1,16-dioxydimethacrylate
DDM: dodecanedioldimethacrylate
CQ: DL-camphorquinone
DABE: ethyl 4-dimethylaminobenzoate
TPO: 2,4,6-trimethylbenzoyldiphenyl-phosphineoxide
Tinuvin 571: 2-(2H-benzotriazol-2-yl)-6-dodecyl-4-methylphenol
BHT: 2,6-di(tert-butyl)hydroxytoluene
Synthesis of the Polysiloxanes
Synthesis of Polysiloxane II 100 g (0.42 mol) of 3-methacryloyloxypropyldimethoxymethylsilane are dissolved in 400 mL of ethyl acetate. 10 mL of 1N HCl solution are added dropwise and the mixture is stirred at 30° C. for 72 h. The mixture is extracted by shaking with 2N NaOH solution, and the organic phase is washed with water and dried over magnesium sulfate. After addition of BHT, the mixture is first concentrated by rotary evaporation at 40° C. and then solvent residues (e.g. water and alcohol residues) are drawn off under reduced pressure by means of an oil pump, in order to remove the alcohol and water residues. This results in a fluid resin having a viscosity of 3 Pa*s at 25° C.

$n_D^{20}$=1.466

Synthesis of Polysiloxane III 100 g (0.40 mol) of 3-methacryloyloxypropyltrimethoxymethylsilane are dissolved in 400 mL of ethyl acetate. 15 mL of 1N HCl solution are added dropwise and the mixture is stirred at 30° C. for 72 h. The mixture is extracted by shaking with 2N NaOH solution, and the organic phase is washed with water and dried over magnesium sulfate. After addition of BHT, the mixture is first concentrated by rotary evaporation at 40° C. and then solvent residues (e.g. water and alcohol residues) are drawn off under reduced pressure by means of an oil pump, in order to remove the alcohol and water residues. This results in a fluid resin having a viscosity of 20 Pa*s at 25° C.

$n_D^{20}$=1.479

Synthesis of Polysiloxane IV
a) Synthesis of a monomeric silane unit (cf. EP 1 685 182 B1, ex. 3):

Added dropwise to an initial charge of 100 g (0.402 mol) of 3-glycidyloxypropyldiethoxymethylsilane under a dry atmosphere are an addition catalyst, BHT as stabilizer and then 38.05 g (0.442 mol) of methacrylic acid, and the mixture is stirred at about 80° C. (about 24 h). The conversion is monitored via the decrease in the carboxylic acid concentration by means of acid titration, and the epoxide conversion by means of Raman spectroscopy/epoxide titration. The band characteristic of the epoxide group is detected in the Raman spectrum at 1256 cm$^{-1}$. The epoxide and carboxylic acid conversions are 99% and 88% respectively (consequence of the carboxylic acid excess).

b) Hydrolysis and condensation of the monomeric silane unit to give a polysiloxane compound (cf. EP 1 685 182 B1, Ex. 6):

After addition of ethyl acetate (1000 mL/mol of monomeric silane unit) and water for hydrolysis with HCl as catalyst to the monomeric silane unit synthesized, the mixture is stirred at 30° C. The progress of the hydrolysis is monitored by water titration. After stirring at 30° C. for several days, the workup is effected by repeatedly extractive shaking with aqueous NaOH, followed by extractive shaking with water and filtration through a hydrophobized filter. After addition of BHT, the mixture is first concentrated by rotary evaporation at 40° C. and then solvent residues (e.g. water and alcohol residues) are drawn off under reduced pressure by means of an oil pump, in order to remove the alcohol and water residues. This results in a fluid resin having a viscosity of 4.5 Pa*s at 25° C.

$n_D^{20}$=1.483

Synthesis of the Disiloxanes

Synthesis of Disiloxane II

Added dropwise to an initial charge of 100 g (0.28 mol) of 1,3-bis(glycidoxypropyl)disiloxane under a dry atmosphere are an addition catalyst, BHT as stabilizer and then 26.10 g (0.30 mol) of methacrylic acid, and the mixture is stirred at about 80° C. (about 24 h). The conversion is monitored via the decrease in the carboxylic acid concentration by means of acid titration, and the epoxide conversion by means of Raman spectroscopy/epoxide titration. The band characteristic of the epoxide group is detected in the Raman spectrum at 1256 cm$^{-1}$. The epoxide and carboxylic acid conversions are 99% and 88% respectively (consequence of the carboxylic acid excess). 300 mL of ethyl acetate are added. This is followed by extractive shaking with 2N NaOH solution, washing with water and drying of the organic phase over magnesium sulfate. After addition of BHT, the solvent is removed under reduced pressure. This results in a mobile resin having a viscosity of 0.3 Pa*s at 25° C.

$n_D^{20}$=1.466

Light-Curing Polysiloxane/Disiloxane Resins (examples 1-4)

CQ and DABE were dissolved in the respective monomers (polysiloxane and disiloxane). The solutions were freed of air at vacuum −0.9 bar. The flexural strength (FS) of the individual resins was determined, and these measurements were used to calculate the modulus of elasticity (MOE).

Surprisingly, a higher modulus of elasticity is found for the mixtures of polysiloxane and disiloxane than for the two respective individual components (FIG. 1). The maximum for the modulus of elasticity was found at a ratio of polysiloxane to disiloxane of about 2:1. A higher modulus of elasticity means that the cured material can offer greater resistance to deformation and hence can better withstand the constant chewing stress.

Example 1

TABLE 1

Composition and properties of poly-/disiloxane resins 1

| | 1-A | 1-B | 1-C | 1-D | 1-E |
|---|---|---|---|---|---|
| Polysiloxane I | 99.25 | 82.71 | 66.17 | 49.625 | 0.00 |
| Disiloxane I | 0.00 | 16.54 | 33.08 | 49.625 | 99.25 |
| CQ | 0.30 | 0.30 | 0.30 | 0.30 | 0.30 |
| DABE | 0.45 | 0.45 | 0.45 | 0.45 | 0.45 |
| FS | 9.9 MPa | 20.8 MPa | 25.2 MPa | 28.2 MPa | 36.3 MPa |
| MOE | 560 MPa | 960 MPa | 1040 MPa | 1020 MPa | 880 MPa |

Example 2

TABLE 2

Composition and properties of poly-/disiloxane resins 2

| | 2-A | 2-B | 2-C | 2-D | 2-E |
|---|---|---|---|---|---|
| Polysiloxane II | 99.25 | 82.71 | 66.17 | 49.625 | 0.00 |
| Disiloxane I | 0.00 | 16.54 | 33.08 | 49.625 | 99.25 |
| CQ | 0.30 | 0.30 | 0.30 | 0.30 | 0.30 |
| DABE | 0.45 | 0.45 | 0.45 | 0.45 | 0.45 |
| FS | 13.0 MPa | 22.3 MPa | 23.0 MPa | 27.8 MPa | 36.3 MPa |
| MOE | 920 MPa | 1140 MPa | 1200 MPa | 1130 MPa | 880 MPa |

Example 3

TABLE 3

Composition and properties of poly-/disiloxane resins 3

| | 3-A | 3-B | 3-C | 3-D | 3-E |
|---|---|---|---|---|---|
| Polysiloxane III | 99.25 | 82.71 | 66.17 | 49.625 | 0.00 |
| Disiloxane I | 0.00 | 16.54 | 33.08 | 49.625 | 99.25 |
| CQ | 0.30 | 0.30 | 0.30 | 0.30 | 0.30 |
| DABE | 0.45 | 0.45 | 0.45 | 0.45 | 0.45 |
| FS | 19.6 MPa | 31.3 MPa | 32.0 MPa | 31.7 MPa | 36.3 MPa |
| MOE | 1050 MPa | 1360 MPa | 1380 MPa | 1250 MPa | 880 MPa |

Example 4

TABLE 4

Composition and properties of poly-/disiloxane resins 4

| | 4-A | 4-B | 4-C | 4-D | 4-E |
|---|---|---|---|---|---|
| Polysiloxane IV | 99.25 | 82.71 | 66.17 | 49.625 | 0.00 |
| Disiloxane II | 0.00 | 16.54 | 33.08 | 49.625 | 99.25 |
| CQ | 0.30 | 0.30 | 0.30 | 0.30 | 0.30 |
| DABE | 0.45 | 0.45 | 0.45 | 0.45 | 0.45 |
| FS | 25.7 MPa | 36.3 MPa | 38.1 MPa | 34.5 MPa | 28.4 MPa |
| MOE | 1260 MPa | 1530 MPa | 1550 MPa | 1470 MPa | 1090 MPa |

Production and Properties of the Composite Pastes (example 5)

For the production of the resin mixtures 5-A to D, TPO, BHT and Tinuvin 571 were each dissolved in the monomers specified and the solutions were freed of air at vacuum −0.9 bar.

For the production of composite pastes 5-E to L, the constituents were each weighed out, homogenized in a SpeedMixer™ DAC 600.1 VAC-P (Hauschild & Co. KG, Hamm, Germany), rolled in a three-roll mill (Exakt, Norderstedt, Germany) and then freed of air in the SpeedMixer™ DAC 600.1 VAC-P at vacuum −0.9 bar.

TABLE 5

Compositions of examples 5-A to F

|  | 5-A | 5-B (comp.) | 5-C | 5-D (comp.) | 5-E | 5-F (comp.) |
|---|---|---|---|---|---|---|
| Polysiloxane IV | 86.76 | 0.00 | 84.90 | 0.00 | 30.05 | 0.00 |
| Disiloxane I | 11.89 | 0.00 | 11.58 | 0.00 | 18.00 | 0.00 |
| Bis-GMA | 0.00 | 40.00 | 0.00 | 39.12 | 0.00 | 15.24 |
| UDMA | 0.00 | 38.65 | 0.00 | 37.79 | 0.00 | 14.72 |
| DDM | 0.00 | 20.00 | 0.00 | 19.57 | 0.00 | 18.09 |
| Barium silicate glass (1.5 μm) silanized | 0.00 | 0.00 | 0.00 | 0.00 | 0.00 | 0.00 |
| Barium silicate glass (0.7 μm) silanized | 0.00 | 0.00 | 0.00 | 0.00 | 24.66 | 24.66 |
| Nanoscale SiO$_2$ (40 nm) silanized | 0.00 | 0.00 | 0.00 | 0.00 | 24.66 | 24.66 |
| TPO | 1.30 | 1.30 | 1.30 | 1.30 | 0.65 | 0.65 |
| Tinuvin 571 | 0.00 | 0.00 | 2.17 | 2.17 | 1.93 | 1.93 |
| BHT | 0.05 | 0.05 | 0.05 | 0.05 | 0.05 | 0.05 |

Compositions of examples 5-G to L

|  | 5-G | 5-H | 5-I | 5-J | 5-K | 5-L (comp.) |
|---|---|---|---|---|---|---|
| Polysiloxane IV | 24.03 | 32.05 | 22.05 | 16.16 | 28.05 | 0.00 |
| Disiloxane I | 14.40 | 16.00 | 14.00 | 10.27 | 8.00 | 0.00 |
| Bis-GMA | 3.05 | 0.00 | 0.00 | 3.05 | 0.00 | 11.43 |
| UDMA | 2.95 | 0.00 | 0.00 | 2.95 | 0.00 | 11.03 |
| DDM | 3.62 | 0.00 | 0.00 | 3.62 | 0.00 | 13.59 |
| Barium silicate glass (1.5 μm) silanized | 0.00 | 16.44 | 32.55 | 32.55 | 32.55 | 32.55 |
| Barium silicate glass (0.7 μm) silanized | 24.66 | 8.22 | 4.11 | 4.11 | 16.44 | 4.11 |
| Nanoscale SiO$_2$ (40 nm) silanized | 24.66 | 24.66 | 24.66 | 24.66 | 12.33 | 24.66 |
| TPO | 0.65 | 0.65 | 0.65 | 0.65 | 0.65 | 0.65 |
| Tinuvin 571 | 1.93 | 1.93 | 1.93 | 1.93 | 1.93 | 1.93 |
| BHT | 0.05 | 0.05 | 0.05 | 0.05 | 0.05 | 0.05 |

TABLE 6

Properties of the compositions of examples 5-A to F

|  | 5-A | 5-B (comp.) | 5-C | 5-D (comp.) | 5-E | 5-F (comp.) |
|---|---|---|---|---|---|---|
| Deviation x | +8.98% | +39.33% | +1.93% | +15.65% | +4.87% | +36.93% |
| Deviation y | +11.49% | +101.83% | +3.72% | +17.92% | +6.69% | +39.31% |
| Viscosity | 3 Pa * s | 3 Pa * s | 3 Pa * s | 3 Pa * s | 5 Pa * s | 10 Pa * s |
| Shrinkage | n.d. | n.d. | n.d. | n.d. | 3.8% | 4.8% |
| FS | n.d. | n.d. | n.d. | n.d. | 55 MPa | 60 MPa |
| MOE | n.d. | n.d. | n.d. | n.d. | 1.5 GPa | 1.6 GPa |

Properties of the compositions of examples 5-G to L

|  | 5-G | 5-H | 5-I | 5-J | 5-K | 5-L (comp.) |
|---|---|---|---|---|---|---|
| Deviation x | +11.72% | +8.59% | +13.58% | +20.34% | +21.54% | +41.85% |
| Deviation y | +12.45% | +9.86% | +14.32% | +22.58% | +22.21% | +43.66% |
| Viscosity | 8 Pa * s | 7 Pa * s | 18 Pa * s | 22 Pa * s | 19 Pa * s | 28 Pa * s |
| Shrinkage | 4.2% | 3.7% | 3.6% | 3.9% | 3.5% | 4.6% |
| FS | 55 MPa | 55 MPa | 85 MPa | 95 MPa | 85 MPa | 100 MPa |
| MOE | 1.5 GPa | 1.5 GPa | 5.0 GPa | 5.2 GPa | 5.5 GPa | 5.3 GPa |

By the use of polysiloxane/disiloxane resins compared to conventional bis-GMA-based resins, it is possible to lower shrinkage and distinctly improve accuracy (lower deviation in the dimensions) in shaped body production. For instance, for the pure resin mixtures, the deviation for the polysiloxane/disiloxane resin 5-A (+9% and +11%) is much better than that for the conventional bis-GMA-based resin 5-B (+39% and +102%). Use of Tinuvin 571 allows the deviation for both resins (5-C and D) to be distinctly lowered. The polysiloxane/disiloxane resin 5-C also gives much better results here, and the bis-GMA-based resin 5-D, in spite of the absorber, still does not attain the accuracy of the polysiloxane/disiloxane resin 5-A without absorber. With rising filler level, the accuracy decreases and the deviation increases. Here too, the polysiloxane/disiloxane resins (5-E and 5-I) give much better results compared to the bis-GMA-based resins (5-F and 5-L), and their shrinkage is lower.

Determination of the Properties:

Flexural strength (FS): The flexural strengths for examples 1-4 were determined in accordance with ISO 4049. The resins were light-cured with a Celalux 2 lamp (VOCO GmbH) section by section for 40 seconds. The flexural strength was determined at an advance rate of 0.75 mm/min on a Zwick universal tester (Zwick GmbH & Co. KG, Ulm). For the determination of the flexural strengths of the examples 5, 10 samples in each case were produced by stereolithography methods with a wavelength of 405 nm (Form 1, Formlabs). The FS samples were cleaned by washing with isopropanol and subsequent drying by means of compressed air, such that no solvent residues remained on the surface. The post-curing was conducted with a Dentacolor XS polymerization unit (Kulzer) for 10 min. All samples were subjected to subsequent sanding with an SiC abrasive paper (P2500 and P4000) for the determination of flexural strength. The flexural strength was determined analogously to examples 1-4 at an advance rate of 0.75 mm/min on a Zwick universal tester (Zwick GmbH & Co. KG, Ulm).

Modulus of elasticity (MOE): The modulus of elasticity is determined from the slope in the elastic range of the force-distance curves from the flexural strength measurements.

Deviation: For the determination of the deviation, the specimens (n=10) from the flexural strength measurements were used prior to sanding. A micrometer screw was used to determine three values in the X direction and three values in the Y direction accurately to ±0.001 mm per specimen.

These values and the specification data of 2.000 mm were used to calculate the deviation.

Shrinkage: Shrinkage was determined by the bonded-disk method of Watts et al. (Watts D C, Cash A J, Determination of polymerization kinetics in visible-light cured materials: Methods development, *Dent Mater* 1991; 7: 281-287). A difference was that exposure was effected with a Celalux 2 lamp (VOCO GmbH) for 40 seconds per measurement.

Viscosity: The viscosity was determined by means of a rheometer (Physica MCR 301) from Anton Paar (Graz, Austria). The measurement is effected at 23° C. in a rotation experiment with plate/plate arrangement (diameter 25 mm, gap 1 mm) in a shear rate range from $10^{-2}$ to $10$ s$^{-1}$. For each measurement, 16 measured values are recorded within an interval of 30 seconds per shear rate. The tables each state the viscosities for the shear rate of $10$ s$^{-1}$.

For additive production of dental moldings, further equipment and methodologies are suitable. For example, it is possible to use equipment such as Perfactory 4 DDP (EnisionTec GmbH), DigitalWax D (DWS Systems), iPro/Pro-Jet/ProX (3D Systems), D30/D30 L (Rapid Shape GmbH) and Freeform (Asiga Global Helpdesk).

We claim:

1. A process for producing a product, the process comprising curing a free radically curable composition comprising
   a) chain-like polysiloxanes, cyclic polysiloxanes, cage type polysiloxanes, mixed forms thereof, or combinations thereof, wherein the polysiloxanes are substituted by free radically polymerizable groups and have at least 3 silicon atoms,
   b) disiloxanes substituted by free radically polymerizable groups and having the following structure:
   $R^1_a R^2_{(3-a)}Si$—O—$SiR^2_{(3-b)}R^1_b$ wherein
   $R^2$ is selected from the group consisting of alkyl, alkenyl, aryl, alkylaryl, and arylalkyl, wherein different $R^2$ may be the same or different,
   $R^1$ is YZ,
   Z is a free radically polymerizable group selected from the structural elements —O—(C=O)—CH=CH$_2$, —O—(C=O)—C(CH$_3$)=CH$_2$, —(C=O)—CH=CH$_2$, —(C=O)—C(CH$_3$)=CH$_2$, —CH=CH$_2$, —C(CH$_3$)=CH$_2$, —NH—(C=O)—CH=CH$_2$ and —NH—(C=O)—C(CH$_3$)=CH$_2$,
   wherein different Z may be the same or different,
   a is 1 or 2,
   b is 1 or 2,
   Y is a connecting element which links the silicon atom to the free radically polymerizable group and consists of an alkylene group,
   wherein the alkylene group is an unsubstituted, linear, straight chain or branched hydrocarbyl chain or
   wherein the alkylene group is an unsubstituted hydrocarbyl group interrupted by a urethane group, urea group, ester group, thiourethane group or amide group or
   wherein the alkylene group is a hydrocarbyl group substituted by a hydroxyl group or this hydroxyl group has been esterified or etherified or
   wherein the alkylene group is a hydrocarbyl group interrupted by an oxygen atom, a nitrogen atom, a sulfur atom, ester groups, thioester groups, or combinations thereof and is substituted by a hydroxyl group or this hydroxyl group has been esterified or etherified, and
   wherein different Y may be the same or different, and
   wherein Y contains 20 or fewer carbon atoms, and
   wherein YZ is chosen such that Z always has a maximum number of atoms,
   c) optionally one, two, three or more free radically curable monomers having no silicon atom,
   d) 85 percent by weight or less of one or more fillers based on the total weight of the free radically curable composition,
   e) initiators, catalysts, or combinations thereof for the free radical polymerization, and
   f) further additives;
wherein the product is produced using an additive manufacturing method.

2. The process of claim 1, wherein the polysiloxanes a) are obtained by hydrolysis or partial hydrolysis and subsequent condensation or co-condensation of one, two, three or more compounds $R^1_a R^2_b SiX_c$ wherein
   X is halogen or alkoxy,
   $R^2$ is selected from the group consisting of alkyl, alkenyl, aryl, alkylaryl, and arylalkyl, wherein different $R^2$ may be the same or different,
   $R^1$ is YZ,
   Z is a free radically polymerizable group selected from the structural elements —O—(C=O)—CH=CH$_2$, —O—(C=O)—C(CH$_3$)=CH$_2$, —(C=O)—CH=CH$_2$, —(C=O)—C(CH$_3$)=CH$_2$, —CH=CH$_2$, —C(CH$_3$)=CH$_2$, —NH—(C=O)—CH=CH$_2$ and —NH—(C=O)—C(CH$_3$)=CH$_2$,
   wherein different Z may be the same or different,
   a is 1 or 2,
   b is 0 or 1,
   c is 2 or 3,
   a +b +c =4,
   Y is a connecting element which links the silicon atom to the free radically polymerizable group and consists of an alkylene group,
   wherein the alkylene group is an unsubstituted, linear, straight chain or branched hydrocarbyl chain or
   wherein the alkylene group is an unsubstituted hydrocarbyl group interrupted by a urethane group, urea group, ester group, thiourethane group or amide group or
   wherein the alkylene group is a hydrocarbyl group substituted by a hydroxyl group or this hydroxyl group has been esterified or etherified or
   wherein the alkylene group is a hydrocarbyl group interrupted by an oxygen atom, a nitrogen atom, a sulfur atom, ester groups, thioester groups, or combinations thereof and is substituted by a hydroxyl group or this hydroxyl group has been esterified or etherified, and
   wherein different Y may be the same or different, and
   wherein Y contains 20 or fewer carbon atoms, and
   wherein YZ is chosen such that Z always has a maximum number of atoms.

3. The process of claim 1, wherein the composition contains:
   constituent a) in an amount of 10%-70% by weight,
   constituent b) in an amount of 2%-40% by weight,
   constituent c) in an amount of 0%-30% by weight, constituent d) in an amount of 0%-85% by weight,
constituent e) in an amount of 0.001%-5% by weight, and
constituent f) in an amount of 0.001%-20% by weight,
and wherein the respective percentages by weight are based on the total mass of the composition.

4. The process of claim 1, wherein the composition contains, as constituent b), 1,3 bis(3-methacryloyloxypropyl)tetramethyldisiloxane.

5. The process of claim 1, wherein the composition does not contain any constituent c).

6. The process of claim 1, wherein the free radically curable composition contains a mixture of fillers d) comprising:
 d1) organically surface modified inorganic nanoparticles having an average particle size of less than 200 nm,
 d2) inorganic microparticles having an average particle size in the range from 0.4μm to 10 μm, and
 d3) optionally further fillers which do not correspond to d1) and d2).

7. The process of claim 6, wherein component d1) is at least partly in nonagglomerated or nonaggregated form.

8. The process of claim 6, wherein component d2) contains two or more micro fractions, wherein a first micro fraction or each of a plurality of first micro fractions has an average particle size in the range from 1 to 10 μm, and wherein a second microparticle fraction or each of a plurality of second microparticle fractions has an average particle size in the range from greater than 0.4μm to less than 1μm.

9. The process of claim 8, wherein the ratio of the total mass of the first microparticle fraction(s) to the total mass of the second microparticle fraction(s) is in the range from 1:1 to 12:1.

10. The process of claim 8, wherein the ratio of the average particle size of the first or a first microparticle fraction to the average particle size of the second or a second microparticle fraction of component d2) is in the range from 1.5:1 to 10:1.

11. The process of claim 6, wherein at least some of the microparticles of component d2) are selected from the group consisting of organically surface modified particles, dental glass particles, and combinations thereof, wherein at least some of the microparticles of component d2) are organically surface modified dental glass particles.

12. The process of claim 6, wherein the composition contains:
 component d1) in an amount of 1%-50% by weight,
 component d2) in an amount of 10%-84% by weight,
 component d3) in an amount of 0%-30% by weight,
 and wherein the percentages by weight are based on the total mass of the free radically curable composition.

13. The process of claim 1, wherein constituent d) contains x ray opaque fractions.

14. The process of claim 13, wherein the x ray opaque fractions are nanoscale $YbF_3$, $BaSO_4$, or combinations thereof.

15. The process of claim 1, wherein the free radically polymerizable groups are acrylate or methacrylate groups.

16. The process of claim 1, wherein the additive manufacturing method is selected from the group consisting of stereolithography, digital light processing, polyjet technology, a galvanometer type scanning method, micro stereolithography, multijet modeling, selective laser sintering, 3D printing, fused deposition modeling, 3D plotting, laminated object manufacturing and film transfer imaging.

17. The process of claim 1, wherein the product is a dental product.

18. The process of claim 17, wherein the dental product is selected from the group consisting of inlays, onlays, veneers, crowns, bridges, artificial teeth, dentures, scaffolds, temporary prostheses, partial prostheses, full prostheses and orthodontic products.

19. The process of claim 1, wherein the composition contains:
 constituent a) in an amount of 10%-35% by weight,
 constituent b) in an amount of 2%-5% by weight,
 constituent c) in an amount of 0%-20% by weight,
 constituent d) in an amount of 40%-78% by weight,
 constituent e) in an amount of 0.1%-2% by weight and
 constituent f) in an amount of 0.001%-10% by weight,
 and wherein the respective percentages by weight are based on the total mass of the composition.

* * * * *